(12) United States Patent
Bertozzi et al.

(10) Patent No.: US 6,465,612 B1
(45) Date of Patent: Oct. 15, 2002

(54) SYNTHETIC PEPTIDES, CONJUGATION REAGENTS AND METHODS

(75) Inventors: Carolyn R. Bertozzi, Albany, CA (US); Lisa A. Marcaurelle, Boston, MA (US); Elena C. Rodriguez, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/405,516

(22) Filed: Sep. 23, 1999

Related U.S. Application Data

(60) Provisional application No. 60/101,494, filed on Sep. 23, 1998.

(51) Int. Cl.[7] .................. A61K 38/00; C07K 14/00; C07K 7/00; C07K 9/00
(52) U.S. Cl. .............. 530/300; 530/305; 530/326; 530/327; 514/2; 514/12; 514/13; 514/14; 514/23; 514/25; 514/42; 435/325; 536/18.6; 560/19
(58) Field of Search ................. 530/326, 300, 530/305, 327; 560/19; 435/325; 536/18.6; 514/2, 12, 13, 14, 23, 25, 42

(56) References Cited

U.S. PATENT DOCUMENTS 4,692,439 A * 9/1987 Rideout et al. ............. 514/185

OTHER PUBLICATIONS

Yu, Zhonghua et al. Irreversible Inhibition of the HIV–1 Protease: Targeting Alkylating Agents to the Catalytic Aspartate Groups. J. Am. Chem. Soc, vol. 118, 1996 pp. 5846–5856, see Scheme 3.

Schmidt, Ulrich et al. The Synthesis of Epnemycin. J. Chem. Soc., Chem. Commun., 1992 pp. 529–530, see Scheme 1.

* cited by examiner

Primary Examiner—Karen Cochrane Carlson
Assistant Examiner—Chih-Min Kam
(74) Attorney, Agent, or Firm—Richard Aron Osman

(57) ABSTRACT

The invention provides methods and compositions useful for making synthetic peptide conjugates. In one embodiment, the invention provides compositions comprising the structure:

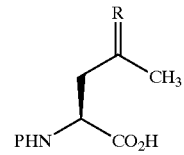

wherein R is selected from lower substituted or unsubstituted alkyl, O, NH and S and P is an amine protection group. In more particular embodiments, the compositions comprise α-amine protected 4,5-dehydroleucine or α-amine protected (2S)-aminolevulinic acid and/or P is F-moc. These compounds may be incorporated into peptides, for example, peptides comprising a substituted or unsubstituted (2S)-aminolevulinic acid residue, such as (2S)-aminolevulinic acid residue is substituted with an O- or N-linked glycoconjugate, or a detectable label.

27 Claims, No Drawings

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      Sequence Peptide

<400> SEQUENCE: 1

Gly Cys Pro Arg Pro Tyr Ser Pro Arg Pro Thr Ser His Pro Arg Pro
  1               5                  10                  15

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      Sequence Peptide

<400> SEQUENCE: 2

Gly Lys Pro Arg Pro Tyr Ser Pro Arg Pro
  1               5                  10

<210> SEQ ID NO 3
<211> LENGTH: 8
<212> TYPE: PRT
<213> ORGANISM: Artificial Sequence
```

-continued

```
<220> FEATURE:
<223> OTHER INFORMATION: Description of Artificial Sequence: Synthetic
      Sequence Peptide

<400> SEQUENCE: 3

Ser His Pro Arg Pro Ile Arg Val
  1               5

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      Sequence Peptide
<221> NAME/KEY: VARIANT
<222> LOCATION: (11)
<223> OTHER INFORMATION: Xaa signifies Thr(alpha-D-GalNAc)

<400> SEQUENCE: 4

Gly Lys Pro Arg Pro Tyr Ser Pro Arg Pro Xaa Ser His Pro Arg Pro
  1               5                  10                  15

Ile Arg Val
```

SYNTHETIC PEPTIDES, CONJUGATION REAGENTS AND METHODS

This application claims priority from provisional patent application No. 60/101,494, filed Sep. 23, 1998, abandoned.

The research carried out in the subject application was supported in part by grants from the National Science Foundation (No. CHE-9734430). The government may have rights in this invention.

FIELD OF THE INVENTION

The invention relates to methods and reagents used to make synthetic peptide conjugates.

BACKGROUND OF THE INVENTION

Glycoprotein pharmaceuticals are major targets of the biotechnology industry and include such widely used therapeutic agents as tissue plasminogen activator (TPA), erythropoietin (EPO) and monoclonal antibodies. Glycosylation presents special challenges in drug discovery and development, largely due to the heterogeneity of oligosaccharide structures obtained from recombinant expression in eukaryotic cell lines. The presence of heterogeneous glycoforms convolutes the characterization of the glycoprotein's structure and biological activity, which hinders clinical evaluation and approval. New strategies for their production which control oligosaccharide structure and uniformity would facilitate the development of glycoprotein pharmaceutical agents.

We have developed novel methods for the synthesis of glycopeptides based on the highly selective reaction of nucleophilic carbohydtrate derivatives with ketone-containing peptides. Peptides bearing unnatural ketone side chains can be generated using N-protected (2S)-aminolevulinic acid by standard solid-phase peptide synthesis (SPPS). Oligosaccharides functionalized at their reducing termini with aminooxy, hydrazide or thiosemicarbazide groups can be coupled to keto-peptides in aqueous solvent without need for protecting groups or auxiliary coupling reagents. These methods can be used to prepare glycopeptides of therapeutic interest.

SUMMARY OF THE INVENTION

The invention provides methods and compositions useful for making synthetic peptide conjugates. In one embodiment, the invention provides compositions comprising the structure:

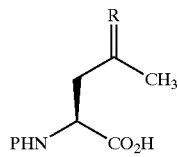

wherein R is selected from lower substituted or unsubstituted alkyl, O, NH and S and P is an amine protection group. In more particular embodiments, the compositions comprise α-amine protected 4,5-dehydroleucine or α-amine protected (2S)-aminolevulinic acid and/or P is F-moc. These compounds may be incorporated into a wide variety of synthetic molecules such as peptides. In a particular embodiment, such peptides comprise a substituted or unsubstituted (2S)-aminolevulinic acid residue, such as (2S)-aminolevulinic acid residue is substituted with an O- or N-linked glycoconjugate, or a detectable label. These peptides may be synthesized in vitro or in vivo and may be incorporated into cells or cellular structures.

The invention also provides methods for conjugating a molecule to a composition comprising a (2S)-aminolevulinic acid residue comprising the step of reacting the molecule with the residue under conditions whereby the molecule is covalently conjugated to residue. In particular embodiments, the composition comprises a synthetic peptide comprising the (2S)-aminolevulinic acid residue or the molecule is a glycoconjugate or comprises a detectable label.

DETAILED DESCRIPTION OF PARTICULAR EMBODIMENTS OF THE INVENTION

The following descriptions of particular embodiments are offered by way of illustration and not by way of limitation. Unless contraindicated or noted otherwise, in these descriptions and throughout this specification, the terms "a" and "an" mean one or more, the term "or" means and/or.

EXAMPLE I

Direct incorporation of unprotected ketone groups into peptides during solid phase synthesis: application of the one-step modification of peptides with two different biophysical probes for FRET.

Abstract: An amino acid bearing an unprotected ketone group, (2S)-aminolevulinic acid, was incorporated into a synthetic peptide using standard Fmoc-based solid-phase methods. The ketone group remained unharmed during the synthesis and provided a uniquely reactive functional group for covalent modification of the peptide. The ketone and the sulfhydryl group of a cysteine residue elsewhere in the peptide were reacted simultaneously with two different biophysical probes, enabling the site-specific installation of a donor and acceptor pair for FRET in one step without the need for differential side chain protection.

Scheme 0

The fluoresence resonance energy transfer (FRET) technique has found widespread use in the study of protein structure and dynamics.[1] The technique requires the installation of two biophysical probes, a donor and an acceptor, at defined locations within the peptide of interest. A number of methods are now available for the conjugation of small molecule probes to peptides and proteins. The majority of these methods are based on coupling electrophilic functional groups, such as α-iodoacetamides[2] and N-hydroxysuccinimido esters,[3] with exposed cysteine and lysine residues, respectively. However, in order achieve site-specific modification of a peptide in the presence of multiple copies of these nucleophilic residues, differential side chain protection must be employed during the synthesis. To avoid the need for extra protecting group manipulations during the conjugation of a synthetic peptide with two different probes, several groups have exploited selective N-terminal reactions,[1f] or incorporated non-native amino acids with suitable photophysical properties (e.g., p-nitrotyrosine) in place of their native counterparts.[4] These approaches are somewhat limited with regard to the site of residence and structure of the probe.

In recent years, the adornment of synthetic peptides with a uniquely reactive electrophile has become an increasingly popular tactic for site-specific modification. For example, ketone or aldehyde groups can be installed in synthetic peptides by conjugating levulinic acid (4-oxopentanoic acid) or masked aldehydes to the ε-amino groups of lysine side chains or to the N-terminus of the peptide.[5] Alternatively, aldehyde groups can be generated by the selective oxidation of N-terminal serine residues with periodate.[6] The ketones or aldehydes form stable covalent adducts with a complementary nucleophile, typically an aminooxy, hydrazide or thiosemicarbazide group, in aqueous milieu in the absence of side chain protecting groups. Still, these methods for decorating peptides with ketones and aldehydes require orthogonal side chain or N-terminal protection for site-specific introduction of the electrophile.

Here we report that (2S)-aminolevulinic acid, an amino acid bearing an unprotected ketone group, can be directly incorporated into synthetic peptides using standard Fmoc-based solid-phase methods. The ketone group survives the synthesis without undergoing any apparent degradation or unwanted side reactions. Furthermore, the ketone is chemically orthogonal to all natural amino acid side chain functional groups. Thus, sulfhydryl groups of cysteine residues, for example, can be modified in the presence of the ketone and vice versa, allowing for the selective labeling of a peptide with two different probes in one synthetic step. The versatility of the ketone group is therefore two-fold: it can be installed at any site along the polypeptide backbone without need for extra protecting group steps, and it does not interfere with reactions involving the nucleophilic functional groups of native amino acid side chains.

Fmoc-protected (2S)-aminolevulinic acid (3) was synthesized in two steps from commercially available 4,5-dehydroleucine[7] (1) as depicted in Scheme 1. The α-amine was first protected with an Fmoc group to afford compound 2,[8] which was then converted to keto-amino acid 3 by reductive ozonolysis.[9] We incorporated compound 3 into a 19-amino acid peptide (4) on an automated peptide synthesizer using standard Fmoc-based solid-phase methods.[10] The sequence of peptide 4 was derived from the antimicrobial glycopeptide drosocin, which is produced by insects in response to immune challenge.[11] The bacteriostatic potency of drosocin is enhanced five-fold by the presence of an O-linked glycan at Thr11, a feature that may reflect an altered conformational preference due to glycosylation. Thus, drosocin constructs labeled with biophysical probes may be useful tools for analyzing the conformation of the unglycosylated peptide compared to the glycosylated version. We chose to install the (2S)-aminolevulinic acid group in place of Ile17. In addition, a cysteine residue was incorporated in place of Lys2 to provide a second orthogonal site for covalent modification.

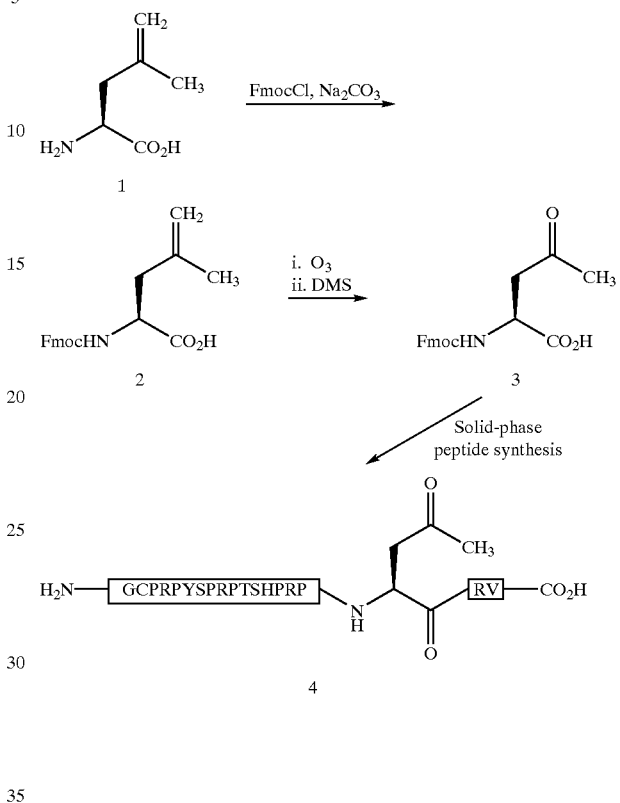

Scheme 1
(the recited amino acid sequence, "GCPRPYSPRPTSHPRP", is SEQ ID NO: 1)

We were concerned that the ketone group might undergo unwanted side reactions, such as condensation with amines to form imines or enamines, or acid- or base-catalyzed aldol condensations, during the process of Fmoc-based solid-phase synthesis. However, the crude product obtained after synthesis and cleavage from the resin was a single peak by reversed-phase HPLC (RP-HPLC) analysis, and its identity as the desired keto-peptide (4) was confirmed by mass spectrometry.[12] No other side products were obtained, indicating that the unprotected ketone group is fully compatible with the reagents of Fmoc-based synthesis, including DCC, piperidine and TFA. In essence, keto-amino acid 3 can be treated similarly to an alanine residue.

To demonstrate the versatility of the ketone group, we modified keto-peptide 4 with two biophysical probes, coumarin iodoacetamide (5) and fluorescein thiosemicarbazide (6), which are commonly used as a donor and acceptor pair for FRET.[13,14] The site-specific labeling of peptide 4 with these probes was achieved in one synthetic step (Scheme 2). Peptide 4 (5 mg) was incubated with 1.2 equivalents each of 5 and 6 in 900 μL DMF and 100 μL of 1.0 M sodium phosphate buffer, pH 7.0. The ligation reaction was complete after 24 hours and the fluorescently labeled peptide (7) was isolated by RP-HPLC and its identity confirmed by mass spectrometry.[15] This general strategy for attaching a pair of small molecules to synthetic peptides is applicable to a wide range of targets.

Scheme 2

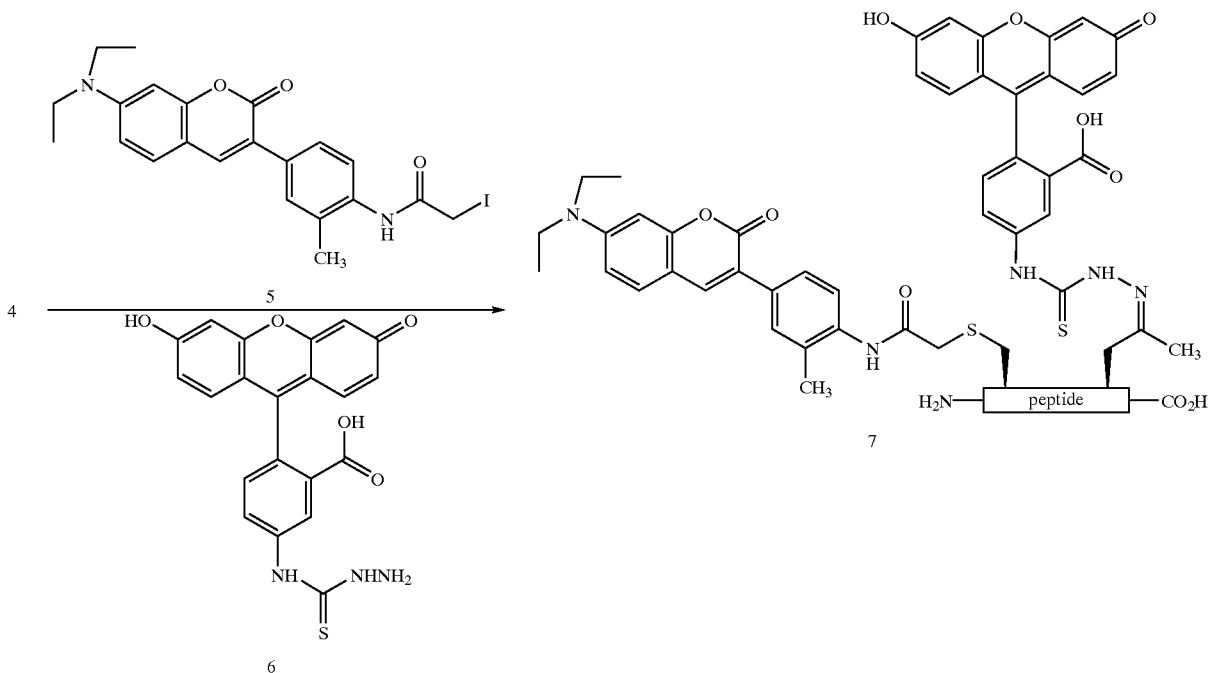

In summary, N-Fmoc-(2S)-aminolevulinic acid (3) can be incorporated into synthetic peptides in an unprotected form to provide a convenient electrophilic functional group, the ketone, for site-specific conjugation. The chemical orthogonality of the ketone to the sulfhydryl group of cysteine side chains allows for the selective modification of peptides with two different probes and facilitates the synthesis of constructs for FRET experiments. This method is therefore a useful complement to traditional protein modification techniques.

REFERENCES AND NOTES 1. (a) Stryer, L. *Ann. Rev. Biochem.* 1978, 47, 819–846. (b) Lee, J. A.; Fortes, P. A. G. *Biochemistry* 1985, 24, 322–330. (c) Taniguchi, K.; Mardh, S. *J. Biol. Chem.* 1993, 268a, 15588–15594. (d) Wu, P.; Brand, L. *Anal. Biochem.* 1994, 218, 1–13. (e) Miki, M.; Kouyama, T. *Biochemistry* 1994, 33, 10171–10177. (f) Imperiali, B.; Rickert, K. W. *Proc. Natl. Acad. Sci.* 1995, 92, 97–101. (g) Xing, J.; Cheung, H. C. *Biochemistry* 1995, 34, 6475–6487. (h) Mehta, S.; Meldal, M.; Ferro, V.; Duus, J. O.; Bock, K. *J. Chem. Soc., Perkins Trans.* 1 1997, 1365–1374. (i) Slevin, P. R. *Meth. Enzynol.* 1995, 246, 300–334.
2. (a) Sharma, J.; Luduena, R. F.; *J. Protein Chem.* 1994, 13, 165–176. (b) Wong, S. Y. C.; Guile, G.; Dwek, R.; Arsequell, G. *Biochem. J.* 1994, 300, 843–850. (c) Esmann, M.; Sar, P. C.; Hideg, K. Marsh, D. *Anal. Biochem.* 1993, 213, 336–348.
3. (a) Bradburne, J. A.; Godfrey, P.; Choi, J. H.; Mathis, J. N. *Appl. Environ. Microbiol,* 1993, 59, 663–668. (b) Fan, J. G.; Pope, L. E.; Vitols, K. S.; Huennekens, F. M. *Biochemistry* 1991, 30, 4573–4580.
4. Meldal, M.; Breddamn, K. *Anal. Biochem.* 1991, 195, 141–147.
5. (a) Canne, L. E.; Ferre-D'Amare, A. R.; Burley, S. K.; Kent, S. B. H. *J. Am. Chem. Soc.* 1995, 117, 2998–3007. (b) Shao, J.; Tam, J. P. *J. Am. Chem. Soc.* 1995, 117, 3893–3899.
6. (a) Geoghegan, K. F.; Stroh, J. G. *Bioconjugate Chem.* 1992, 3, 138–146. (b) Rose, K. *J. Am. Chem. Soc.* 1994, 116, 30–33. (c) Rose, K.; Zeng, W.; Regamey, P. -O.; Chernushevich, I. V.; Standing, K. G.; Gaertner, H. F. *Bioconjugate Chem.* 1996, 7, 552–556.
7. 4,5-Dehydroleucine (1) was purchased from Bachem.
8. Hardy, P. M.; Sheppard, P. W. *J. Chem. Soc., Perkin Trans.* 1 1983, 723–729.
9. Preparation of N-Fmoc-(2S)-aminolevulinic acid (3): A solution of Fmoc-4,5-dehydroleucine (2)[8] (1.1 g, 3.1 mmol) in 9:1 $CH_2Cl_2$/methanol (15 mL) was cooled to −78° C. and purged with $N_2$ for 10 min. A stream of ozone was passed through the solution until a blue color persisted. The reaction mixture was then purged with $N_2$ (ca. 10 min) until the solution was no longer blue in color. Dimethylsulfide (0.58 mL, 7.9 mmol) was added and the solution was warmed to rt overnight. Excess dimethylsulfide and solvent were removed in vacuo and the resulting yellow syrup was purified by silica gel chromatography (10:1 $CHCl_3$/methanol, 0.1% AcOH) and crystallized from $CH_2Cl_2$/hexanes to afford 0.89 g (81%) of compound 3 as a white solid: mp 136–138_C; $^1$H NMR (300 MHz, $CDCl_3$): δ7.76 (d, 2 H, J=7.4), 7.58 (d, 2 H, J=5.1), 7.39 (t, 2 H, J=7.0), 7.30 (dt, 2H, J=6.2, 1.2), 5.85 (d, 1 H, J=7.8, N-H), 4.60 (m, 1H), 4.43–4.34 (m, 1H), 4.22 (t, 1 H, J=6.9), 3.25 (dd, 1H, J=18.3, 4.0), 2.99 (dd, 1H J=15.5, 4.0), 2.19 (s, 3H, $CH_3$); $C^{13}$ NMR (100 MHz, $CDCl_3$): δ175.5, 156.2, 143.7, 143.6, 141.2, 127.7, 127.0, 125.0, 120.0, 119.8, 67.3, 49.5, 47.0, 45.0; FAB-HRMS calcd for $C_{20}H_{20}NO_5$ (M+H$^+$) 354.1341, found 354.1334.
10. Fields, G. B.; Noble, R. L. *Int. J. Peptide Protein Res.* 1990, 35, 161–214.
11. (a) Bulet, P.; Dimarcaq, J.-L.; Hetru, C.; Lagueux, M.; Charlet, M.; Hegy, G.; Dorsselar, A. V.; Hoffman, J. A. *J. Biol. Chem.* 1993, 268, 14893–14897. (b) Bulet, P.; Urge, L.; Ohresser, S.; Hetru, C.; Otvos, L. *Eur. J. Biochem.* 1996, 238, 64–69.

12. ES-MS: calcd for peptide 4 (M+H$^+$) 2173, found m/z 2173.
13. Coumarin iodoacetamide and flourescein thiosemicarbazide were purchased from Molecular Probes (cat. # C-404 and F-121, respectively).
14. (a) Haugland, R. *Molecular Probes Handbook of Fluorescent Probes and Research Chemicals;* 6th ed. 1996. (b) Theilen, T. P. G. M.; Maassen, J. A.; Kriek, J.; Moller, W. *Biochemistry* 1984, 23, 6668–6674. (c) Odom, O. W.; Deng, H. Y.; Dabbs, E. R.; Hardesty, B. *Biochemistry* 1984, 23, 5069–5076.
15. Reversed-phase ($C_{18}$) HPLC conditions: Elution gradient: $CH_3CN$ (B) in $H_2O$ (A), both with 0.1% TFA (10⌀60% B, over 50 min). ES-MS: calcd for peptide 7 (M+H$^+$) 2939, found m/z 2939.

EXAMPLE II

Synthesis of an oxime-linked neoglycopeptide with glycosylation-dependent activity similar to its native counterpart.

Abstract: Neoglycopeptides containing an oxime sugar-peptide linkage can be generated by coupling an aminooxy sugar with a peptide bearing a keto-amino acid. The coupling reaction can be executed in aqueous milieu without need for protecting groups on the peptide or saccharide, or auxiliary coupling reagents. Using this method, an oxime-linked analog of an antimicrobial peptide with glycosylation-dependent function was prepared and found to have similar bioactivity to the native glycopeptide. Thus, replacement of the sugar-peptide bond with an unnatural but synthetically facile linkage can produce functional neoglycopeptides.

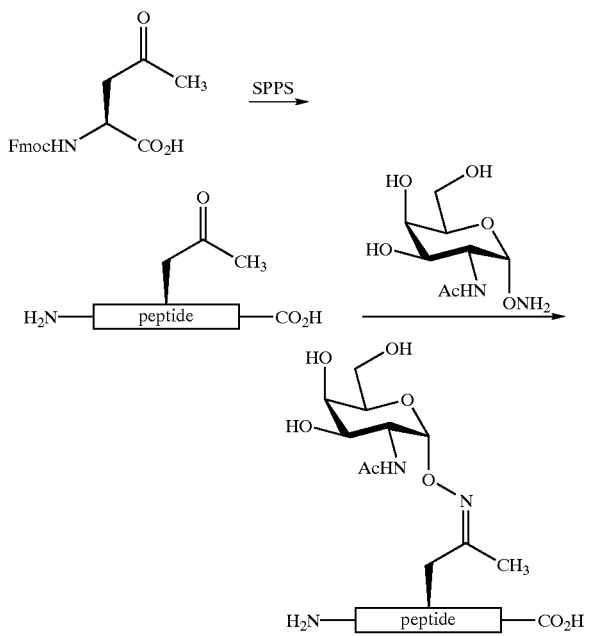

An appealing strategy for the assembly of glycopeptides is the convergent coupling of an oligosaccharide with a pre-formed peptide. While this strategy has been implemented in the synthesis of N-linked glycopeptides,[1] O-linked glycopeptides have been prohibitive due to the difficulty in forming a glycosidic bond in the presence of multifunctional proteins and carbohydrates. However, if the native glycosidic linkage between the sugar and the peptide backbone were replaced with an alternate non-native linkage, a convergent synthesis of O-linked glycopeptides could be realized. To date, this strategy has not been widely explored, perhaps due to the suggestion that the proximal GalNAc residue of O-linked glycoproteins plays a role in modulating local peptide conformnation.[2] However, the importance of the native sugar-peptide linkage for the bioactivity of O-linked glycopeptides, especially those with glycosylation-dependent function, has yet to be addressed. It may be that in some cases this linkage can be substituted without dramatically altering global structure or function. The complexity of glycopeptide synthesis could certainly be reduced by replacing the sugar-peptide linkage with a more facile bond.

We synthesized an O-linked glycopeptide with glycosylation-dependent activity (1) and a neoglycopeptide analog (2) in which the sugar and peptide are linked by an oxime (Formulae 1 a). Glycopeptide 1, named drosocin, is an antimicrobial substance produced by insects in response to immune challenge, and its potency in blocking bacterial growth is enhanced approximately five-fold by the presence of a GalNAc residue at Thr11.[3] A similar glycosylation-induced enhancement in potency is observed for other drosocin glycoforms,[3,4] suggesting that the glycan exerts a conformational influence on the peptide.

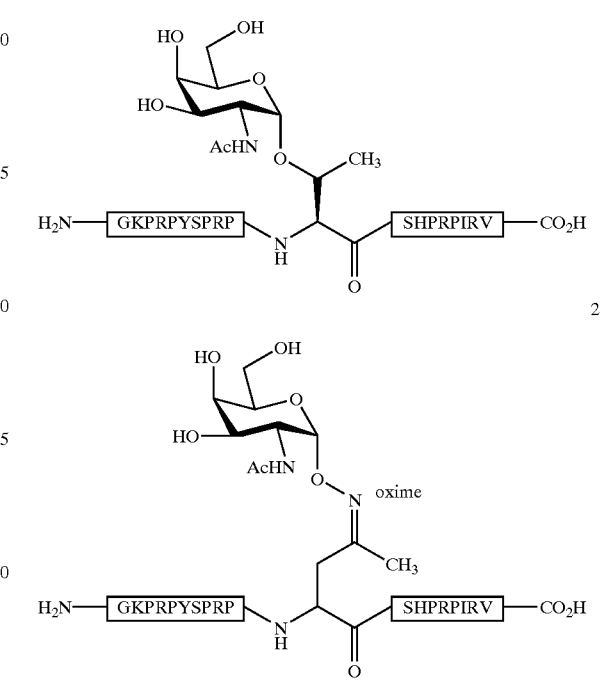

Formulae 1a. Native drosocin (1), bearing a proximal GalNAc residue attached in an α-glycosidic linkage to Thr11, and a drosocin neoglycopeptide (2) bearing an oxime-linked α-GalNAc residue. The recited amino acid sequence, "GKPRPYSPRP", is SEQ ID NO:2, and the sequence "SHPRPIRV" is SEQ ID NO:3.

We envisioned that the oxime-linked neoglycopeptide (2) could be obtained from the highly selective reaction of an aminooxy sugar with a peptide bearing an unnatural ketone side chain. The ketone group is chemically orthogonal to all natural amino acid side chains and reacts with aminooxy groups in a highly specific manner, allowing site-specific conjugation without the requirement for protecting groups on the sugar or peptide. While methods for the synthesis of neoglycopeptides bearing other nominative linkages are well known,[5] the majority of these methods involve the coupling of electrophilic carbohydrate derivatives with nucleophilic amino acids. For example, bromoacetamides[5d] or isothiocyanates[5e] can be coupled with exposed cysteine or lysine residues, respectively. However, in the presence of several copies of these nucleophilic residues, such methods are not site selective.

As described elsewhere herein, unprotected ketone groups can be incorporated into a peptide using Fmoc-protected (2S)-aminolevulinic acid (3) by solid-phase peptide synthesis (SPPS) (Scheme 1a). We generated keto-drosocin (4) in this fashion, in which the (2S)-aminolevulinic acid residue replaced Thr11, the natural site of glycosylation.

Scheme 1a
(the recited amino acid sequence, "GCPRPYSPRPTSHPRP", is SEQ ID NO: 2, and the sequence "SHPRPIRV" is SEQ ID NO:3)

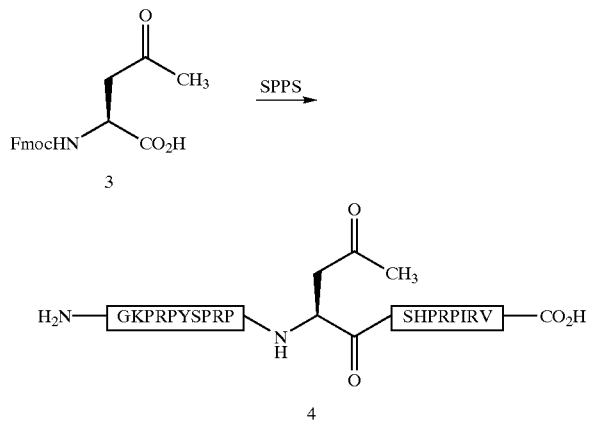

The aminooxy sugar, α-GalNAc derivative 7 (Scheme 2), was generated from glycosyl chloride 5[7] using a method similar to that reported by Roy and coworkers.[8] Compound 5 was reacted with N-hydroxysuccinimide (NHS) to afford the α-NHS glycoside 6. Reductive acetylation of the azide, followed by deprotection of the acetyl esters and succinimido group provided the desired aminooxy sugar (7).[9]

Scheme 2a

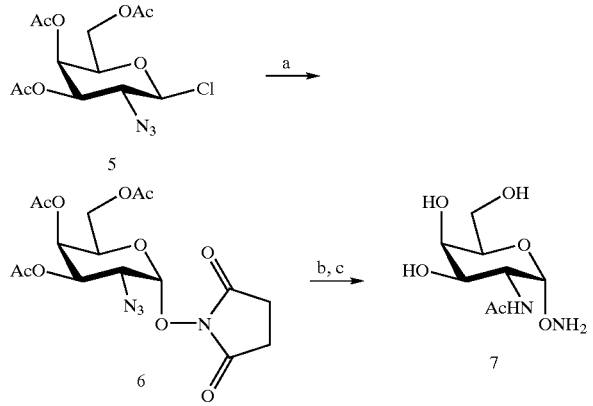

Reagents and conditions: (a) N-hydroxysuccinimide, Bu$_4$N (HSO$_4$), 1:1 CH$_2$Cl$_2$/1 M Na$_2$CO$_3$, 52%; (b) H$_2$, 10% Pd/C, Ac$_2$O, 100%; (c) H$_2$N$_4$ ⊃ H$_2$O, 71%.

The coupling reaction of keto-drosocin (4) with aminooxy GalNAc (7) was carried out in 1.0 M NaOAc buffer, pH 5.5 at 37° C. (Formulae 2a). The progress of the reaction was monitored by reversed-phase HPLC. The reaction was essentially complete after eight hours, as indicated by the presence of a single peak in the HPLC trace. No significant byproducts were observed. and the identity of the drosocin neoglycopeptide (2) was confirmed by electrospray ionization mass spectrometry (ESI-MS).

In order to evaluate the functional consequences of replacing the glycosidic linkage at Thr11 with an unnatural oxime linkage, we evaluated the bacteriostatic activity of neoglycopeptide 2 and compared its activity to both native (1) and unglycosylated drosocin.[10] The oxime-linked neoglycopeptide (2) was found to be four-fold more potent in blocking bacterial growth (IC$_{50}$=0.16±0.04 μM) than unglycosylated drosocin (IC$_{50}$=0.63±0.05 μM), and similar in potency to native drosocin (1) (IC$_{50}$=0.10±0.02 μM). These results indicate that the native sugar-peptide linkage in drosocin is not essential to achieve glycosylation-dependent enhancement in potency. Analagous results are obtained with other O-linked glycopeptides.

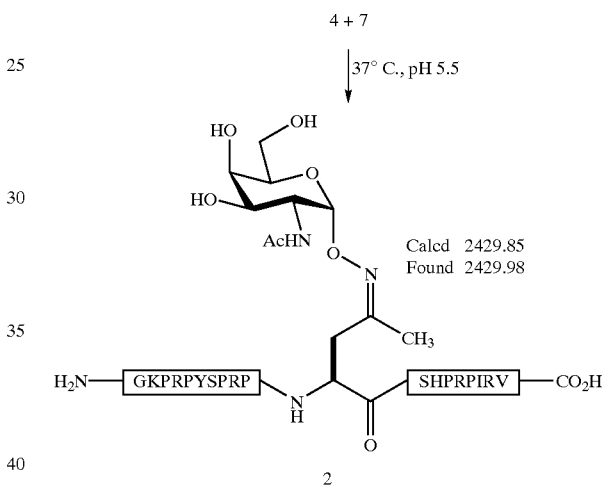

Formulae 2a. Coupling reaction of keto-drosocin (4) with aminooxy GalNAc (7) to give oxime-linked neoglycopeptide 2. The recited amino acid sequence, "GKPRPYSPRP", is SEQ ID NO:2, and the sequence "SHPRPIRV" is SEQ ID NO:3.

In summary, we have shown that a functional neoglycopeptide can be synthesized by the condensation of an aminooxy sugar with a keto-peptide. There are several convenient features of this approach. First, this method obviates the need for the cunibsersome assembly of glycosylated amino acids typically used in the synthesis of native O-linked glycopeptides.[11] Second, the carbohydrate can be installed at a user-defined location within any given peptide without concern for differential protection of amino acid side chains. Third, the highly selective coupling reaction is carried out under aqueous conditions without use of auxiliary coupling reagents. Furthermore, the only byproduct of the reaction is water, minimizing the need for purification. Finally, a variety of neoglycopeptides can be obtained from a single keto-peptide using this convergent synthetic strategy.

REFERENCES AND NOTES 1. (a) Anisfeld, S. T.; Lansbury, J. P. T. *J. Org. Chem.* 1990, 55, 5560–5562. (b) Cohen-Anisfeld, S. T.; Lansbury, J. P.

T. J. Am. Chem. Soc. 1993, 115, 10531–10537. (c) Roberge, J.; Beebe, X.; Danishefsky, S. J.; *Science* 1995, 269, 202–204. (d) Danishefsky, S. J.; Hu, S.; Cirillo, P. F.; Eckhardt, M.; Seeberger, P. *Chem. Eur. J.* 1997, 3, 1617–1628.
2. (a) Andreotti, A. H.; Kahne, D. *J. Am. Chem. Soc.* 1993, 115, 3352–3353. (b) Liang, R.; Andreotti, A. H.; Kahne, D. *J. Am. Chem. Soc.* 1995, 117, 10395–10396. (c) Maeji, N. J.; Inoue, Y.; Chûjô, R. *Biopolymers* 1987, 26, 1753–1767.
3. (a) Bulet, P.; Urge, L.; Ohresser, S.; Hetru, C.; Otvos, L. *Eur. J. Biochem.* 1996, 238, 64–69. (b) Bulet, P.; Dimarcq, J.-L.; Hetru, C.; Languex, M.; Charlet, M.; Hegy, G.; Dorsselar, A. V.; Hoffman, J. A. *J. Biol. Chem.* 1993, 268, 14893–14897.
4. Rodriguez, E. C.; Winans, K. A.; King, D. S.; Bertozzi, C. R. *J. Am. Chem. Soc.* 1997, 119, 9905–9906.
5. (a) Stowell, C. P.; Lee, Y. C. *Neoglycoproteins: The Preparation and Application of Synthetic Glycoproteins;* Academic Press: San Francisco, 1980; Vol. 37, pp 225–281. (b) Mangusson, G.; Chemack, A. Y.; Kihlberg, J.; Kononov, L. O. *Synthesis of Neoglycoconjugates;* Academic Press: San Diego, 1994. (c) Lee, Y. C.; Lee, R. T. *Meth. Enzymol.* 1994, 242, 3–123. (d) Wong, S. Y. C.; Guile, G.; Dwek, R.; Arsequell, G. *Biochem. J.* 1994, 300, 843–850. (e) Mulins, R. E.; Langdon, R. G. *Biochemistry* 1980, 19, 1199–1205.
6. Marcaurelle, L. A.; Bertozzi, C. R., preceeding paper.
7. Lemieux, R. U.; Ratcliffe, R. M. *Can. J. Chem.* 1979, 57, 1244–1251.
8. Cao, S.; Tropper, F. D.; Roy, R. *Tetrahedron* 1995, 51, 6679–6686.
9. Characterization of aminooxy-2-acetamido-2-deoxy-α-D-galactopyranoside (7): $^1$H NMR (300 MHz, D$_2$O): δ4.97 (d, 1 H, J=4.0), 4.23 (dd, 1 H, J=11.3, 4.0), 4.00 (m, 2 H), 3.81 (m, 3 H), 2.06 (s, 3 H); $^{13}$C NMR (100 MHz,): δ174.55, 100.55, 70.93, 68.34, 67.49, 61.07, 49.11, 21.83; FAB-HRMS calcd for C$_8$H$_{17}$N$_2$O$_6$ (M+H$^+$) 237.1087, found 237.1084.
10. The growth inhibition assay was performed essentially as described by Bulet et al.[3] Sterile 96-well plates were used, with a final volume of 100 μL per well. This volume consisted of 90 μL of mid-logarithmnic phase culture of *E. coli* D22 in LB media containing streptomycin (50 μg/mL), added to 10 μL of serially diluted peptide (native drosocin (1), unglycosylated drosocin or neoglycopeptide 2) in water. Final peptide concentrations ranged from 10$^{-8}$ to 10$^{-5}$ M. Plates were incubated for 24 h at rt. Bacterial growth was determined by measuring the absorbance at 415 nm on a BioRad 550 microplate reader. Measurements were taken at t=0 h and t=24 h, and the change in absorbance (optical density) was recorded.
11. (a) Meldal, M.; St. Hiliare, P. M. *Curr. Opin. Chem. Biol.* 1997, 1, 552–563. (b) Mathieux, N.; Paulsen, H.; Meldal, M.; Block, K. *J. Chem. Soc., Perkin Trans. 1* 1997, 2259–2364. (c) Sames, D.; Chen, X.-T.; Danishefsky, S. J. *Nature* 1997, 389, 587–591.

EXAMPLE III

Aminooxy, hydrazide and theosemicarbazide-functionalized saccharides: versatile reagents for glycoconjugate synthesis.

ABSTRACT: Saccharides functionalized at their reducing termini with aminooxy, hydrazide or thiosemicarbazide groups are versatile reagents for the synthesis of glycoconjugates using chemoselective ligation reactions. They can be prepared from aminoglycosides without the requirement for protecting groups on the saccharide. Novel neoglycopeptides were constructed by the condensation of aminooxy and thiosemicarbazide-functionalized oligosaccharides with ketone groups on an unprotected peptide scaffold. In this fashion, we synthesized neoglycopeptides bearing the chitobiosyl moiety found in N-linked glycopeptides, or a sialyl Lewis x motif found in O-linked glycopeptides.

Organic chemists have exercised significant creativity in the construction of glycoconjugate assemblies as tools for studying carbohydrate recognition and as potential therapeutic agents.[1] These synthetic accomplishments, which include neoglycoproteins[2], glycodendrimers[3], glycolipo-somes[4] and glycopolymers[5], have been sparked by the growing realization that glycoconjugates participate in a wide range of normal and pathophysiological processes.[6] Given the importance of glycoconjugates as tools for glycobiology and as emerging pharmaceutical reagents, new methods for attaching sugars to scaffolds are of significant current interest.

The highly selective condensation reactions of ketones or aldehydes with aminooxy, hydrazide or thiosemicarbazide groups (forming oximes, hydrazones and thiosemicarbazones, respectively) are popular for the conjugation of peptides and proteins.[7,8] The reactions proceed in aqueous solvent and their high selectivity obviates the requirement for protection of other functional groups on the coupling partners. Despite the utility of these 'chemoselective ligation' reactions[7,8] in the assembly of peptide-based macromolecules, their implementation in glycoconjugate synthesis is limited to a few examples.[9] The majority of current methods for attaching sugars to scaffolds involve the coupling of electrophilic carbohydrate derivatives with exposed thiol or amino groups. The electrophilic derivatives include α-haloacetamides,[10] bromoethyl glycosides,[11] maleimides,[12] and isothiocyanates.[13] Here we report an alternate ligation strategy based on the coupling of nucleophilic carbohydrate derivatives to synthetic scaffolds. We synthesized carbohydrates bearing aminooxy, hydrazide or thiosemicarbazide groups at their reducing termini, and coupled two of these derivatives to ketone groups on a peptide scaffold. The novel neoglycopeptides produced in this fashion have structural motifs shared by native N-linked or O-linked glycopeptides.[14]

The direct attachment of an aminooxy group to the reducing terminus of a mono- or disaccharide can be accomplished by formation of the N-hydroxysuccinimido (NHS) glycoside[15] followed by cleavage of the succinimide group with hydrazine, a strategy first reported by Roy and coworkers.[15b] Accordingly, we synthesized β-linked aminooxy analogs of galactose (4), N-acetylglucosamine (GlcNAc) (5) and lactose (6) from the corresponding protected NHS glycosides 1, 2 and 3, respectively (Scheme 1b). In addition, we prepared an α-aminooxy GalNAc derivative (8) to mimic of the peptide-proximal α-GalNAc residue found in O-linked glycoproteins. This was achieved by first generating the α-NHS glycoside of peracetylated 2-azido-2-deoxy galactose by reaction of azido chloride 7[16] with NHS. Subsequent reductive acetylation of the azide and deprotection with hydrazine furnished the desired analog.[17]

The simple aminooxy sugars 4–6 and 8 can be transformed into more complex oligosaccharides using established enzymatic methods.[18] As an example, we synthesized an aminooxy-functionalized analog of the tetrasaccharide sialyl Lewis x (NeuAcα2ø3Galβ1ø4(Fucα1ø3)GlcNAc), a motif recognized by the selectin family of adhesion molecules that has been explored as a selectin inhibitor in the form of many different conjugated assemblies.[19] Aminooxy lactose (6) was converted to the corresponding sialyllactose analog using an α(2,3)-sialyltransferase (α(2,3)-ST) and the glycosyl donor CMP-sialic acid. Without isolation, aminooxy sialyllactose was fucosylated using an α(1,3)-fucosyltransferase (α(1,3)-FucT) with GDP-fucose as the glycosyl donor affording sialyl Lewis x analog 9 (Scheme 2b).[20,21] The presence of the aminooxy group did not adversely affect the course of the enzymatic reactions.

In order to generate complex oligosaccharide coupling partners without the use of glycosyltransferases, we required a strategy for functionalizing the reducing terminus with minimal protecting group manipulations. We therefore developed methods for the synthesis of aminooxy, hydrazide and thiosemicarbazide-functionalized sugars that employ the well-known Kochetkov procedure[22] for generating glycosylamines from unprotected free-reducing sugars. β-Amino lactose (10) was prepared by stirring the free disaccharide in a concentrated solution of $NH_4HCO_3$.[22b] Aminooxy and hydrazide groups were then introduced as depicted in Scheme 3b. Compound 10 was coupled with N-(t-butoxycarbonyl)aminooxyacetic acid and subsequently deprotected with TFA to give aminooxy sugar 12. The coupling reaction of 10 with monomethyl succinate, followed by treatment with hydrazine gave hydrazide 14.

The most efficiently prepared saccharide derivatives for chemoselective ligation reactions were glycosyl thiosemicarbazides, prepared from the corresponding isothiocyanates[23] as shown in Scheme3b. β-Amino lactose (10) was reacted with thiophosgene[24] in aqueous solution to give the corresponding isothiocyanate (16). Without isolation, the isothiocyanate (16) was immediately converted to thiosemicarbazide 18 by treatment with hydrazine. The same procedure when applied to β-amino chitobiose (15)[24a] furnished thiosemicarbazide 19. The overall yields of the isolated thiosemicarbazides ranged from 50–70%. The synthesis of compound 19 highlights the utility of this procedure for transforming small amounts of precious oligosaccharides into suitable coupling partners.

Finally, we constructed neoglycopeptides containing motifs found in naturally occurring N- and O-linked glycopeptides by coupling the nucleophilic sugars to a synthetic peptide fashioned with a ketone group (20, Formulae 1b). Keto-peptide 20 was synthesized by the direct incorporation of (2S)-aminolevulinic acid into the peptide during Fmoc-based solid-phase synthesis, a procedure we have recently reported.[24] We reacted keto-peptide 20 with chitobiose thiosemicarbazide (19) to afford neoglycopeptide 21, a structure that resembles the core chitobiosyl-asparagine motif shared by all N-linked glycoproteins (Formulae 1b).[25] The coupling reaction of keto-peptide 20 with aminooxy sialyl Lewis x analog 9 produced neoglycopeptide 22, which resembles the O-linked glycopeptides that function as native selectin ligands.[26] It should be emphasized that these condensation reactions proceed in aqueous solvent without need for auxiliary reagents. In addition, subsequent purification is straightforward as the only other product of the reaction is water. The facile construction of neoglycopeptides related to native N- and O-linked structures underscores the utility of this approach for glycoconjugate synthesis.

Synthetic procedures for compounds 4–6, 8, 9, 12, 14, 18 and 19:

General methods: All chemical reagents were obtained from commercial suppliers and used without further purification. α(2,3)-Sialyltransferase, α(1,3)-ficosyltransferase, CMP-sialic acid and GDP-fucose were purchased from Calbiochem. Flash chromatography was performed using 230–400 mesh silica gel 60 (E. Merck No 9385). Analytical thin layer chromatography (tlc) was conducted on Analtech Uniplate silica gel plates with detection by ceric ammonium molybdate, p-anisaldehyde, ninhydrin and/or UV light. Unless otherwise specified, all reactions were conducted at rt. High-pressure liquid chromatography (HPLC) was performed on a Rainin Dynamax SD-200 system using Microsorb and Dynamax aminopropyl and $C_{18}$ columns (particle size 5 μm; analytical column: 4.6 mm ID×25 cm, 1 mL/min; semi-preparative column: 10 mm ID×25 cm, 3 mL/min), and UV detection (200 or 230 nm) was performed with a Rainin Dynamax UV-1 detector. It is important to note that use of low wavelengths (200 nm) was important for detecting aminooxy sugar derivatives which have very low extinction coefficients. The $^1H$- and $^{13}C$-NMR spectra were obtained at either 400 or 500 MHz with Bruker AMX-400 and DRX-500 spectrometers. Chemical shifts are reported in δ values downfield from tetramethylsilane (TMS) and coupling constants are reported in Hz.

Aminooxy-β-D-galactopyranoside (4). Compound 1 (1.0 g, 2.2 mmol) was dissolved in 25 mL of $N_2H_4.H_2O_x$ (55%) and the solution was stirred at rt overnight. The reaction mixture was concentrated in vacuo, filtered and purified by HPLC on aminopropyl silica gel (200 nm detection) using a gradient of $CH_3CN:H_2O$ (100:0⌀55:45 over 60 min) to provide 0.38 g (86%) of 4. (The product has low UV absorbtivity relative to the other products, butanedioic hydrazide and acetyl hydrazide, and tends to elute closely following butanedioic hydrazide during HPLC purification). $^1H$-NMR (400 MHz, $D_2O$): δ3.50 (app t, 1 H, J=9.0), 3.65 (dd, 1 H, J=6.8,9.9), 3.70 (m, 3 H), 3.90 (d, 1 H, J=3.3), 4.50 (d, 1 H, J=8.1); $^{13}C$-NMR (100 MHz, $D_2O$): δ63.58, 71.14, 71.89, 75.35, 77.65, 108.11; FAB-HRMS (M+H$^+$) calcd for $C_6H_{14}NO_6$ 196.0821, found 196.0819.

Aminooxy-2-acetamido-2-deoxy-β-D-glucopyranoside (5). Compound 2 (100 mg, 0.2 mmol) was dissolved in 20 mL of $N_2H_4.H_2O_x$ (55%) and the solution was stirred at rt overnight. The reaction mixture was concentrated in vacuo, filtered and purified by aminopropyl silica gel HPLC (200 nm detection) using a gradient of $CH_3CN:H_2O$ (100:0⌀60:40 over 75 min) to provide 29 mg (55%) of 5. $^1H$-NMR (500 MHz, $D_2O$): δ2.01 (s, 3 H), 3.43 (m, 2 H), 3.52 (app t, 1 H, J=8.6), 3.69 (dd, 1 H, J=9.1, 10.5), 3.73 (dd, 1 H, J=5.5, 12.3), 3.91 (dd, 1 H, J=1.8, 12.2), 4.75 (d, 1 H, J=8.8); $^{13}C$-NMR (125 MHz, $D_2O$): δ22.01, 53.74, 60.58, 69.67, 73.69, 75.71, 103.55, 174.69; FAB-HRMS (M+H$^+$) calcd for $C_8H_{17}N_2O_6$ 237.1087, found 237.1082.

Aminooxy-β-D-lactoside (6). Compound 3 (0.50 g, 0.68 mmol) was dissolved in 6.8 mL of $N_2H_4.H_2O_x$ (55%) and the solution was stirred at rt overnight. The reaction was concentrated in vacuo, filtered and purified by aminopropyl silica gel HPLC (200 nm detection) using a gradient of $CH_3CN:H_2O$ (100:0⌀50:50 over 90 min) to provide 0.20 g (81%) of 6. $^1H$-NMR (500 MHz, $D_2O$): δ3.33 (app t, 1 H, J=9.2), 3.52 (dd, 1 H, J=7.8, 9.9), 3.81–3.60 (m, 8 H), 3.90 (d, 1 H, J=3.3), 3.98 (dd, 1 H, J=2.1, 12.3), 4.42 (d, 1 H, J=7.8), 4.57 (d, 1 H, J=8.3); $^{13}C$-NMR (100 MHz, $D_2O$): δ60.15, 61.12, 68.65, 71.05, 71.46, 72.62, 74.53, 74.81, 75.45, 78.30, 103.03, 104.94; FAB-HRMS (M+H$^+$) calcd for $C_{12}H_{24}NO_{11}$ 358.1349, found 358.1350.

2-Azido-2-deoxy-3,4,6-tri-O-acetyl-α-D-galactopyranosyl hydroxysuccin-imide (8a). To a solution of N-hydroxysuccinimide (1.3 g, 7.5 mmol) and tetrabutylammonium hydrogensulfate (0.79 g, 2.3 mmol) in 1 M $Na_2CO_3$ (11.5 mL) was added a solution of 7 (0.81 g, 2.3 mmol) in $CH_2Cl_2$(11.5 mL). The biphasic mixture was stirred vigorously for 24 h, diluted with $CH_2Cl_2$ (50 mL), and washed with H$_2$O (2×25 mL) and brine (40 mL). The aqueous layers were extracted with CH$_2$Cl$_2$, and the combined organic layers were dried (Na$_2$SO$_4$) and concentrated in vacuo. The crude product was purified by silica gel chromatography (100:1 CHCl$_3$/MeOH) to yield 0.41 g (52%) of 8a as mixture of anomers (4:1 α/β). The α-anomer was isolated as a white solid upon trituration with CH$_2$Cl$_2$/hexanes. $^1$H-NMR (500 MHz, CDCl$_3$): δ2.05 (s, 3 H), 2.07 (s, 3 H), 2.15 (s, 3 H), 2.77 (s, 4 H), 3.92 (m, 2 H), 4.21 (dd, 1 H, J=6.5, 11.3), 5.09 (app t, 1 H, J=7.2), 5.45 (dd, 1 H, J=3.2, 11.5), 5.52 (d, 1 H, J=3.7), 5.56 (dd, 1 H, J=1.4, 3.1); $^{13}$C-NMR (125 MHz, CDCl$_3$): δ22.11, 22.22, 26.81, 57.10, 61.59, 67.56, 67.91, 69.18, 101.51, 167.00, 167.32, 167.80, 167.86; FAB-MS: Calcd. for C$_{16}$H$_{20}$N$_4$O$_{10}$ 428, found m/z 429 (M+H$^+$). Anal. Calcd. for C$_{16}$H$_{20}$N$_4$O$_{10}$: C, 44.86; H, 4.71; N, 13.08. Found: C, 44.82; H, 4.54; N, 13.03.

2-Acetamido-2-deoxy-3,4,6,-tri-O-acetyl-α-D-galactopyranosyl hydroxy-succinimide (8b). To a solution of 8a (56 mg, 0.13 mmol) and 10% Pd/C (11 mg) in 1:1 MeOH/CH$_2$Cl$_2$ (3 mL) was added acetic anhydride (25 μL, 0.26 mmol). The mixture was stirred under an atmosphere of H$_2$ gas at rt. After 3.5 h, the reaction mixture was filtered through Celite and concentrated in vacuo to give 58 mg (100%) of compound 8b. $^1$H-NMR (500 MHz, CDCl$_3$): δ2.00 (s, 3 H), 2.04 (s, 3 H), 2.07 (s, 3 H), 2.15 (s, 3 H), 2.73 (s, 4 H), 3.93 (dd, 1 H, J=6.7, 11.4), 4.25 (dd, 1 H, J=5.9, 11.4), 4.73 (td, 1 H, J=3.7, 9.6), 4.97 (t, 1 H, J=6.0), 5.28 (m, 2 H), 5.51 (d, 1 H, J=1.9), 6.10 (d, 1 H, J=9.5); $^{13}$C-NMR (125 MHz, CDCl$_3$): δ20.66, 20.72, 23.14, 25.37, 47.15, 61.59, 67.12, 67.31, 69.21, 104.20, 170.11, 170.44, 170.58, 170.61, 170.86; FAB-HRMS (M+H$^+$) calcd. for C$_{18}$H$_{24}$N$_2$O$_{11}$ 445.1458, found 445.1467.

Aminooxy 2-acetamido-2-deoxy-α-D-galactopyranoside (8). Compound 8b (57 mg, 0.13 mmol) was dissolved in 5 mL of N$_2$H$_4$.H$_2$O$_x$ (55%) and the solution was stirred at rt overnight. The solution was concentrated in vacuo, filtered and purified by aminopropyl silica gel HPLC (200 nm detection) using a gradient of CH$_3$CN:H$_2$O (90:10ø65:35 over 60 min) to provide 26 mg (85%) of 8. $^1$H-NMR (500 MHz, CDCl$_3$): δ2.06 (s, 3 H), 3.81 (m, 3 H), 4.00 (m, 2 H), 4.23 (dd, 1 H, J=4.0, 11.3), 4.97 (d, 1 H, J=4.0); $^{13}$C-NMR (125 MHz, CDCl$_3$): δ21.83, 49.11, 61.07, 67.49,68.35, 70.93, 100.54, 174.56; FAB-HRMS (M+H$^{30}$) calcd for C$_8$H$_{17}$N$_2$O$_6$ 237.1087, found 237.1084.

Aminooxy sialyl Lewis x analog (9). To 5 mg of 7 (0.014 mmol) was added in succession water (105 μL), 0.5 M HEPES (14 μL, pH 7.4), 25% Triton CF-54 (2.8 μL), and 5% BSA (2.2 μL). To this solution was added CMP-sialic acid (10 mg, 0.014 mmol) followed by α(2,3)-sialyltransferase (12.5 μL, 1 mU/μL), and calf intestinal alkaline phosphatase (CIAP) (2.9 μL, 1 U/μL, Sigma). The reaction was incubated for 5 d at rt. To the reaction mixture was then added water (18 μL), 0.5 M HEPES (5 μL, pH 7.4), 1.0 M MnCl$_2$ (1 μL), and GDP-fucose (9 mg, 0.014 mmol). α(2-3)-Fucosyltransferase (E.C. 2.4.1.65) (25 mL, 0.5 mU/mL) and CIAP (1 μL) were added and the reaction was incubated at rt for an additional 5 d. The solution was filtered through an Amicon 3 kDa membrane and purified by aminopropyl silica gel HPLC (195 nm detection) eluting with 74:26 CH$_3$CN/15 mM KH$_2$PO$_4$, pH 5.2, to provide compound 9. Due to the presence of buffer salts in the eluant, an isolated yield could not be accurately determined, but HPLC analysis of the enzymatic reactions indicated approximately 60% conversion to 9. $^1$H-NMR (500 MHz, D$_2$O): δ1.17 (d, 1 H, J=6.7), 1.79 (t, 1 H, J=12.1), 2.03 (s, 3 H, NHCOCH$_3$), 2.76 (dd, 1 H, H-3"$_{eq}$, J$_{3"eq,4"}$=4.6, J$_{3"eq,3"ax}$=12.5), 3.34 (br t, 1 H, H-2), 3.94 (d, 1 H, H-4', J$_{4',3'}$=3.3) 4.02 (dd, 1 H, H-6$_a$, J$_{6a,5}$=2.1, J$_{6a,6b}$=12.3), 4.08 (dd, 1 H, H-3', J=3.2, J$_{3',2'}$=10.0), 4.49 (d, 1 H, H-1, J$_{1,2}$=7.8), 4.59 (d, 1 H, H-1', J$_{1',2'}$=8.3), 5.43 (d, 1 H, J=4.0).

Compound 11. To a solution of N-(t-butoxycarbonyl) aminooxyacetic acid (31 mg, 0.16 mmol) in DMSO (1 mL) was added DIEA (76 mL, 0.44 mmol), compound 10 (50 mg, 0.15 mmol), and BOP (80 mg, 0.17 mmol) in succession. The clear yellow solution was stirred at rt for 2 h. The crude product was precipitated from solution by the addition of 1:2 acetone/ether (12 mL), incubation at −20° C. for 15 min and centrifugation. A second batch of product was obtained by precipitation from the concentrated supernatant. The pooled precipitate was purified by aminopropyl silica gel HPLC (200 nm detection) using a gradient of CH$_3$CN:H$_2$O (100:0ø35:65 over 60 min) to provide 31 mg (41%) of compound 11. $^1$H-NMR (500 MHz, D$_2$O): δ1.48 (s, 9 H), 3.54 (m, 2 H), 3.75 (m, 9 H), 3.94 (m, 2 H), 4.47 (m, 3 H), 5.07 (d, 1 H, J=9.2); $^{13}$C-NMR (125 MHz, D$_2$O): δ27.30, 58.78, 60.98, 68.42, 70.86, 71.43, 72.42, 74.54, 74.90, 75.29, 76.43, 77.66, 78.77, 84.02, 84.02, 102.79, 158.60, 172.34; FAB-HRMS (M+H$^+$) calcd for C$_{19}$H$_{35}$N$_2$O$_{14}$ 515.2088, found 515.2090.

Compound 12. Compound 11 (27 mg, 0.053 mmol) was dissolved in 3:2 CH$_2$Cl$_2$/TFA (2 mL) and stirred at rt for 1.5 h. The solvent was removed under vacuum and crude product was dissolved in water, neutralized using weak anion exchange resin (Amberlyst) and concentrated to afford 21 mg (100%) of 12. $^1$H-NMR (500 MHz, D$_2$O): δ3.56 (m, 2 H), 3.77 (m, 11 H), 3.94 (m, 2 H), 4.29 (d, 2 H, J=0.8), 4.47 (d, 1 H, J=2.6) 5.08 (d, 1 H, J=9.2); $^{13}$C-NMR (125 MHz, D$_2$O): δ59.71, 60.96, 68.46, 70.84, 71.29, 72.39, 73.47, 74.90, 75.26, 76.40, 77.58, 78.79, 102.77, 173.82; FAB-HRMS (M+H$^+$) calcd for C$_{14}$H$_{27}$N$_2$O$_{12}$ 415.1564, found 415.1559.

Compound 13. To a solution of monomethylsuccinate (22 mg, 0.16 mmol) in DMSO (1 mL) was added DIEA (76 mL, 0.44 mmol), glycosylamine 10 (50 mg, 0.15 mmol), and BOP (80 mg, 0.17 mmol) in succession. The clear yellow solution was stirred at rt for 2 h. The crude product was precipitated from solution by the addition of 1:2 acetone/ether (12 mL), incubation at −20° C. for 15 min and centrifugation. The pooled precipitate was purified by aminopropyl silica gel HPLC (200 nm detection) using a gradient of CH$_3$CN:H$_2$O (100:0ø35:65 over 60 min) to provide 32 mg (48%) of compound 13. $^1$H-NMR (500 MHz, D$_2$O): δ2.68 (m, 4 H), 3.45 (app t, 1 H, J=9.1), 3.56 (dd, 1 H, J=7.8, 9.8), 3.74 (m, 14 H), 3.94 (m, 2 H), 4.46 (d, 1 H. J=7.8) 4.99 (d, 1 H, J=9.2); $^{13}$C-NMR (125 MHz, D$_2$O): δ28.71, 30.08, 52.27, 59.81, 60.98, 68.49, 70.88, 71.41, 72.44, 75.00, 75.29, 76.28, 77.72, 79.04, 102.80, 175.58, 176.01; HRMS (M+H$^+$) calcd for C$_{15}$H$_{28}$N$_4$O$_{12}$ 456.1704, found 456.1708.

Lactose succinic hydrazide (14). Compound 13 (31 mg, 0.67 mmol) was dissolved in 2 mL of N$_2$H$_4$.H$_2$O$_x$ (55%) and the solution was stirred at rt overnight. The reaction was concentrated in vacuo, filtered and purified by aminopropyl silica gel HPLC (200 nm detection) using a gradient of CH$_3$CN:H$_2$O (90:10ø65:35 over 60 min) to provide 18 mg (59%) of 14. $^1$H-NMR (500 MHz, D$_2$O): δ2.52 (app t, 2 H, J=6.9), 2.64 (m, 2 H), 3.44 (app t, 1 H, J=9.0), 3.56 (dd, 1 H, J=7.9, 8.8), 3.75 (m, 14 H), 3.94 (m, 3 H), 4.46 (d, 1 H, J=7.7) 4.98 (d, 1 H, J=9.2); $^{13}$C-NMR (125 MHz, D$_2$O): δ28.54, 30.63, 59.78, 60.97, 68.47, 70.86, 71.39, 72.42, 74.96, 75.28, 76.28, 77.67, 79.01, 102.78, 173.62, 175.85; FAB-HRMS (M+H$^+$) calcd for C$_{16}$H$_{30}$N$_3$O$_{12}$ 456.1829, found 456.1826.

Lactose thiosemicarbazide (18). To a solution of 10 (50 mg, 0.15 mmol) in 3 mL of 0.3 M NaHCO$_3$ was added thiophosgene (33 μL, 0.44 mmol). The orange solution was stirred at rt for 20 min during which the glycosyl isothiocyanate (16) was produced in quantitative yield as determined by tlc analysis. To this solution was added 26 μL (0.45 mmol) of $N_2H_4.H_2O_x$ (55%) resulting in a bright yellow solution. This solution was stirred for 20 min at rt then concentrated in vacuo. Subsequent HPLC purification on aminopropyl silica gel [$CH_3CN:H_2O$ (90:10ø65:35 over 60 min)] afforded 29 mg (48%) of thiosemicarbazide 18. $^1$H-NMR (500 MHz, $D_2O$): δ3.57 (dd, 1 H, J=7.8, 9.9), 3.76 (m, 9 H), 3.95 (m, 2 H), 4.48 (d, 1 H, J=7.8) 5.54 (br d, 1 H, J=8.5); $^{13}$C-NMR (125 MHz, $D_2O$): δ59.71, 60.98, 68.49, 70.87, 71.58, 72.42, 74.92, 75.28, 76.20, 77.79, 83.24, 102.82; HRMS (M+H$^+$) calcd for $C_{13}H_{26}N_3O_{10}S$ 416.1339, found 416.1338. Appropriate precautions should be taken to avoid contact with thiophosgene; it is a highly toxic and corrosive reagent.

Chitobiose thiosemicarbazide (19). To a solution of β-amino chitobiose 15 (9.0 mg, 0.021 mmol) in 0.3 M $NaHCO_3$ (0.5 mL) was added thiophosgene (5.1 μL, 0.067 mmol). The orange solution was stirred at rt for 30 min to give the glycosyl isothiocyanate (17) in quantitative yield as determined by tlc analysis. To the solution was then added 3.9 μL (0.070 mmol) of $N_2H_4.H_2O$, (55% ) resulting in a bright yellow solution. This solution was stirred for 10 min at rt then concentrated in vacuo. Subsequent HPLC purification on aminopropyl silica gel [$CH_3CN:H_2O$ (90:10ø65:35 over 60 min)] afforded 6.6 mg (62%) of thiosemicarbazide 19. $^1$H-NMR (500 MHz, $D_2O$): δ2.00 (s, 3 H), 2.07 (s, 3 H), 3.72 (m, 12 H), 4.61 (d, 1 H, J=8.5) 5.52 (d, 1 H, J=9.6); $^{13}$C-NMR (125 MHz, $D_2O$): δ21.79, 22.01, 53.76, 55.50, 59.91, 60.44, 69.62, 72.34, 73.34, 75.80, 75.93, 78.95, 82.52, 101.36, 174.55, 174.86; FAB-HRMS (M+H$^+$) calcd for $C_{17}H_{32}N_5O_{10}S$ 498.1870, found 498.1869. Appropriate precautions should be taken to avoid contact with thiophosgene; it is a highly toxic and corrosive reagent Synthesis of neoglycopeptides 21 and 22. To 50 μL of keto-peptide 20 (50 mM) was added 10 μL of 1 M NaOAc buffer (pH 5.5) and 40 μL of 19 or 9 (100 mM). The reaction mixture was incubated at 37C. for 24 h and the corresponding product (21 or 22, respectively) was isolated by RP-HPLC with a gradient of $CH_3CN$: $H_2O$, both with 0.1%. TFA (10:90ø30:60 over 30 min). ESI-MS: Glycopeptide 21: calcd 2690.0 (M+H$^+$), found 2986.9. Glycopeptide 22: calcd 2987.3 (M+H$^+$), found 2986.9, calcd 3009.3 (M+Na$^+$), found 3009.1.

Compound 11. To a solution of N-(t-butoxycarbonyl) aminooxyacetic acid (31 mg, 0.16 mmol) in DMSO (1 mL) was added DIEA (76 mL, 0.44 mmol), compound 10 (50 mg, 0.15 mmol), and BOP (80 mg, 0.17 mmol) in succession. The clear yellow solution was stirred at rt for 2 h. The crude product was precipitated from solution by the addition of 1:2 acetone/ether (12 mL), incubation at −20°C. for 15 min and centrifugation. A second batch of product was obtained by precipitation from the concentrated supernatant. The pooled precipate was purified by aminopropy silica gel HPLC (200 nm detection) using a gradient of $CH_3CN:H_2O$ (100:0ø35:65 over 60 min) to provide 31 mg (41%) of compound 11. $^1$H-NMR (500 MHz, $D_2O$): δ1.48 (s, 9 H), 3.54 (m, 2 H), 3.75 (m, 9 H), 3.94 (m, 2 H), 4.47 (m, 3 H), 5.07 (d, 1 H, J=9.2); $^{13}$C-NMR (125 MHz, $D_2O$): δ27.30, 58.78, 60.98, 68.42, 70.86, 71.43, 72.42, 74.54, 74.90, 75.29, 76.43, 77.66, 78.77, 84.02, 84.02, 102.79, 158.60, 172.34; FAB-HRMS (M+H$^+$) calcd for $C_{19}H_{35}N_2O_{14}$ 515.2088, found 515.2090.

REFERENCES 1. (a) Roy, R. *Curr. Opin. Struct. Biol.* 1996, 6, 696. (b) Roy, R. Sialoside Mimetics and Conjugates as Anti-Inflammatory Agents and Inhibitors of Flu Virus Infections. *In Carbohydrates in Drug Design;* Witczak, Z. J.; Nieforth, K. A., Eds.; Marcel Dekker: New York, 1997; Chapter 3, pp 83–135.
2. Lee, Y. C.; Lee, R. T. *Meth. Enzymol.* 1994, 242, 3 and references cited therein.
3. (a) Palcic, M. M.; Hong, L.; Zanini, D.; Bhella, R. S.; Roy, R. *Carbohydr. Res.* 1998, 305, 433. (b) Zanini, D.; Roy, R. *J. Org. Chem.* 1998, 63, 3486 and references cited therein.
4. (a) Reichert, A.; Nagy, J. O.; Spevak, W.; Charych, D. *J. Am. Chem. Soc.* 1995, 117, 829. (b) Spevak, D.; Foxall, C.; Charych, D. H.; Dasgupta, F.; Nagy, J. O. *J. Med. Chem.* 1996, 39, 1018.
5. (a) Manning, D. D.; Strong, L. E.; Hu, X.; Beck, P. J.; Kiessling, L. L. *Tetrahedron* 1997, 53, 11937. (b) Roy, R.; Tropper, F. D.; Romanowski, A. *Bioconjugate Chem.* 1992, 3, 265.
6. Varki, A. *Glycobiol.* 1993, 3, 97 and references cited therein.
7. Muir, T. W. *Structure* 1995, 3, 649.
8. Lemieux, G. A.; Bertozzi, C. R. *Trends Biotechnol.* 1998, 16(12):506–13.
9. (a) Rodriguez, E. C.; Winans, K. A.; King, D. S.; Bertozzi, C. R. *J. Am. Chem. Soc.* 1997, 119, 9905; (b) Cervigni, S. E.; Dumy, P.; Mutter, M. *Angew. Chem., Int. Ed. Engl.* 1996, 35, 1230; (c) Zhao, Y.; Kent, S. B. H.; Chait, B. T. *Proc. Natl. Acad. Sci. U.S.A.* 1997, 94, 1629.
10. (a) Wong, S. Y. C.; Guile, G. R.; Dwek, R. A.; Arsequell, G. *Biochem. J.* 1994, 300, 843; (b) Davis, N. J.; Flitsch, S. L. *Tetrahedron Lett.* 1991, 32, 6793.
11. Bengtsson, M.; Broddefalk, J.; Dahmen, J.; Henriksson, K.; Kihlberg, J.; Lonn, H.; Srinivasa, B. R.; Stenvall, K. *Glycoconjugate J.* 1998, 15, 223.
12. Hansen, P. R.; Olsen, C. E.; Holm, A. *Biooconjugate Chem.* 1998, 9, 126.
13. (a) Mullins, R. E.; Langdon, R. G. *Biochemistry* 1980, 19, 1199; (b) For a review on glycosyl isothiocyanates see, Witczak, Z. J. *Adv. Carbohydr. Chem. Biochem.* 1986, 44, 91.
14. For a review on the synthesis of native glycopeptides see, Large, D. G.; Warren, C. D. *Glycopeptides and Related Compounds: Synthesis, Analysis, and Applications;* Marcel Dekker: New York, 1997.
15. (a) Andersson, M.; Oscarson, S. *Glycocnjugate J.* 1992, 9, 122; (b) Cao, S.; Tropper, F. D.; Roy, R. *Tetrahedron* 1995, 51, 6679.
16. Lemieux, R. U.; Ratcliffe, R. M. *Can. J. Chem.* 1979, 57, 1244.
17. Saccharides with hydrazine attached at the reducing terminus, or glycosylhydrazines, have also been reported. They react with aldehydes to form hydrazones, but the glycosidic linkage hydrolyzes in water after several hours. By contrast, we have found aminooxy sugars to be stable for months in aqueous solution. (a) Takasaki, S.; Mizuochi, T.; Kobata, A. *Meth. Enzymol.* 1982, 83, 263; (b) Tolvanen, M.; Gahmberg, C. G. *J. Biol. Chem.* 1986, 261, 9546.
18. (a) Palcic, M. M. *Meth. Enzymol.* 1994, 230, 300; (b) McGarvey, G. J.; Glenn, J.; Wong, C. -H. *Liebigs Ann.* 1997, 1059.
19. Simanek, E. E.; McGarvey, G. J.; Jablonowski, J. A.; Wong, C. -H. *Chem. Rev.* 1998, 98, 833.
20. The enzymatic reactions were executed essentially as described in Ichikawa, Y.; Lin, Y.-C.; Dumas, D. P.; Shen, G.-J.; Garcia-Junceda, E.; Williams, M. A.; Bayer, R.; Ketcham, C.; Walker, L. E.; Paulson, J. C.; Wong, C. -H. *J. Am. Chem. Soc.* 1992, 114, 9283.

21. The α(2,3)-ST and α(1,3)-FucT were purchased from Calbiochem.
22. (a) Likhosherstov, L. M.; Novikova, O. S.; Derevitskaja, V. A.; Kochetkov, N. K. *Carbohydr. Res.* 1986, 146, C1; (b) Vetter, D.; Gallop, M. A. *Bioconjugate Chem.* 1995, 6, 316; (c) Meinjohanns, E.; Meldal, M.; Paulsen, H.; Dwek, R. A. *J. Chem. Soc., Perkin Trans.* 1 1998, 549.
23. Unprotected glycosyl isothiocyanates have been used for protein modification (ref. 13), but their conversion to glycosyl thiosemicarbazides has not to our knowledge been reported.
24. Marcaurelle, L. A.; Bertozzi, C. R., *Tetrahedron Lett.*, in press.
25. Coupling reactions were performed in 1 M NaOAc buffer, pH 5.5, 37° C. The neoglycopeptide products were purified by RP-HPLC and characterized by ES-MS. The yields of the coupling reactions ranged from 85 to 95%.
26. Rosen, S. D.; Bertozzi, C. R. *Curr. Biol.* 1996, 6, 261.

Scheme 1b

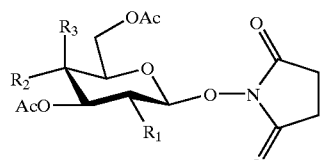

1 R₁ = OAc, R₂ = H, R₃ = OAc
2 R₁ = NHAc, R₂ = OAc, R₃ = H
3 R₁ = OAc, R₂ = β-Gal(OAc)₄, R₃ = H

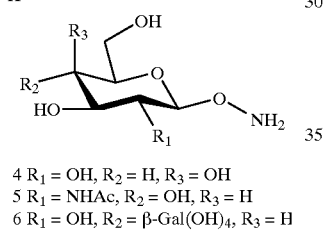

4 R₁ = OH, R₂ = H, R₃ = OH
5 R₁ = NHAc, R₂ = OH, R₃ = H
6 R₁ = OH, R₂ = β-Gal(OH)₄, R₃ = H

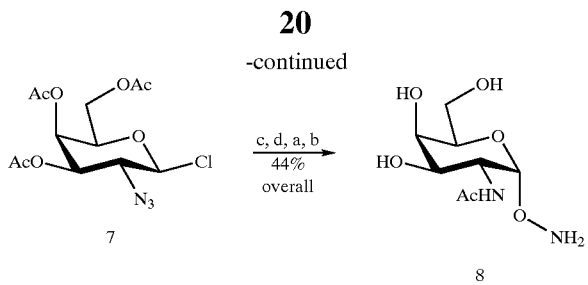

$^a$(a) N₂H₄·H₂O, 14 h; (b) HPLC on aminopropyl silica gel;
(c) NHS, Bu₄N(HSO₄), 1:1 CH₂Cl₂/1M Na₂CO₃, 24 h;
(d) H₂, 10% Pd/C, Ac₂O, 4 h.

Scheme 2b

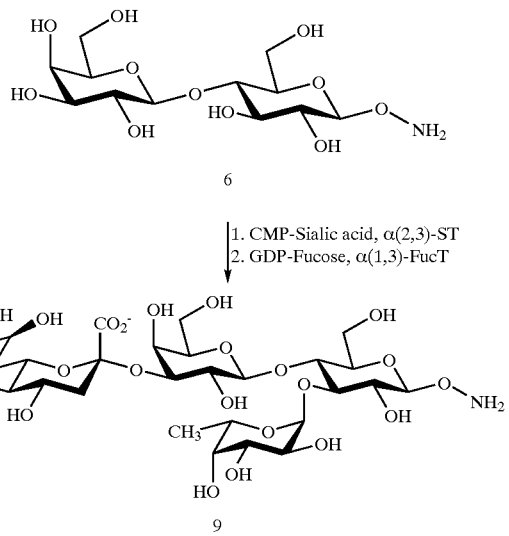

Scheme 3b

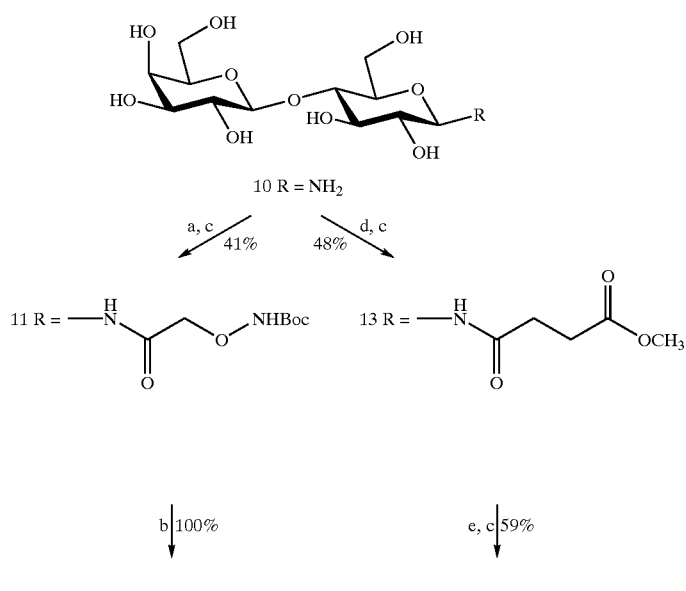

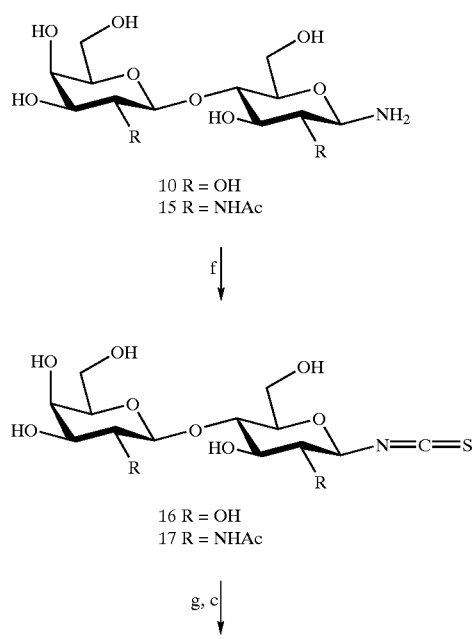

-continued

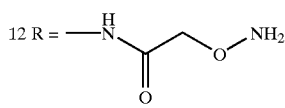 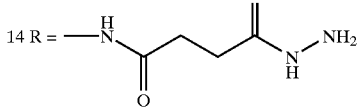 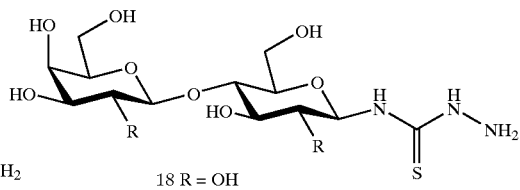

50–70% isolated yields a(a) BocNHOCH$_2$CO$_2$H, DIEA, BOP, 2 h;
(b) TFA, 1.5 h;
(c) HPLC on aminopropyl silica gel;
(d) monomethyl succinate, DIEA, BOP, 2 h;
(e) N$_2$H$_4$•H$_2$O, 18 h;
(f) Cl$_2$CS, 0.3 M NaHCO$_3$, 20 min;
(g) N$_2$H$_4$•H$_2$O, 10 min.

Formulae 1b (the recited amino acid sequence, "GKPRPYSPRP", is SEQ ID NO:2, and the sequence "SHPRPIRV" is SEQ ID NO:3)

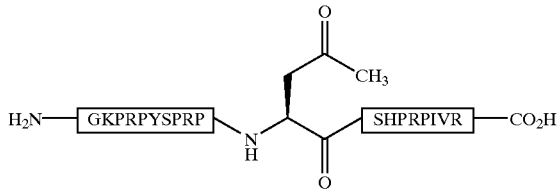

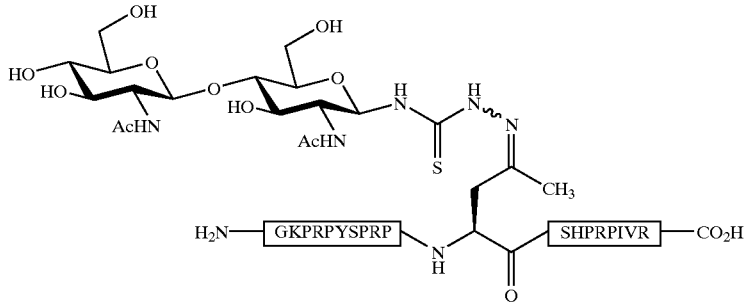

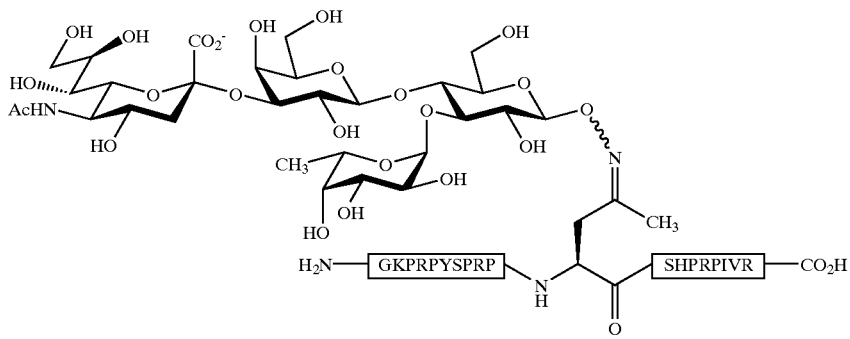

EXAMPLE IV

A strategy for the chemoselective synthesis of )-linked glycopeptides with native sugar-peptide linkages.

ABSTRACT: The convergent coupling of oligosaccharides to a protein scaffold is an attractive approach to the synthesis of complex glycopeptides. Here we describe a strategy for the convergent assembly of O-linked glycopeptide analogs using the principle of chemoselective ligation. A single GalNAc residue was incorporated into a glycopeptide by solid phase methods, and then oxidized to the corresponding aldehyde with the enzyme galactose oxidase. Hydroxylamine-fimctionalized sugars were ligated onto the glycopeptide aldehyde affording oxime-linked products with native sugar-peptide linkages. This strategy was demonstrated in the synthesis of chemoselectively ligated analogs of the antibacterial glycopeptide drosocin.

The critical role of specific oligosaccharide structures in the biological fimction of many glycoproteins is now well appreciated.[1] The importance of protein-bound oligosaccharides in cell-cell recognition events,[2] and in modulating protein folding and stability[3] has been highlighted in a number of recent landmark studies, inspiring the development of new synthetic methods for the construction of glycoproteins with defined, homogeneous glycoforms. Many of the difficulties inherent to the synthesis of such complex molecules, including the requirement for extensive protecting group manipulations and the chemical sensitivity of glycosidic linkages, have been elegantly addressed by several groups.[4,5] Yet, the convergent coupling of tailor-made oligosaccharides to a protein scaffold, an appealing strategy for the synthesis of complex glycoproteins, has been successful only in the construction of the amide sugar-peptide linkage found in N-linked glycopeptides. The extension of this approach to O-linked glycopeptides has been hindered by the difficulties endemic to the formation of a sugar-peptide glycosidic bond.

Here we report a strategy for the convergent synthesis of O-linked glycopeptide analogs with native sugar-peptide linkages using the principle of chemoselective ligation.[6] At the heart of this approach is the introduction of mutually and uniquely reactive functional groups (e.g., an aldehyde group and a hydroxylamino group) onto unprotected fragments and the coupling of these fragments in an aqueous environment. First, building block 1 [N$^\alpha$-Fmoc-Thr/Ser(Ac$_3$-α-D-GalNAc)] is incorporated into a glycopeptide by solid phase peptide synthesis (SPPS).[4c-j] Next, a chemically unique functional group for chemoselective ligation is introduced using the commercially available enzyme galactose oxidase,[7] which selectively converts galactose or GalNAc residus to the corresponding C-6 aldehydes. The aldehyde groups are reacted with an unprotected oligosaccharide bearing a hydroxylamino group at the reducing end, affording an oxime-linked analog of the β1ø6 glycosidic linkage that is frequently observed in naturally occurring O-linked glycans.[8] This approach allows flexibility in the elaboration of outlying glycoforms while retaining the native proximal GalNAc-α-Ser/Thr linkage.

Our focus on preserving the sugar-peptide linkage was motivated by several studies suggesting a major role for the proximal GalNAc residue in modulating local peptide conformation.[9] In some glycopeptide targets, perturbation of this linkage might result in loss of native conformation and therefore function. Several methods are available for the covalent attachment of oligosaccharides to peptides through non-native linkages,[10] including chemoselective ligation of the reducing terminal aldehyde of an oligosaccharide to an N-terminal hydroxylarnino group.[11] These methods may not be suitable, however, for the synthesis of glycoproteins with glycosylation-dependent active conformations.

To demonstrate this methodology we selected the insect-derived, antibacterial 19-amino acid glycopeptide drosocin, the biological activity of which is influenced by glycosylation.[12] Drosocin's potency in blocking bacterial growth is enhanced 2–8 fold (depending on the target bacterial strain) by a single O-linked disaccharide (GaløGalNAc) at Thr11.[13] Threonine derivative 1$^{4h}$ was incorporated into drosocin using Fmoc-based solid-phase methods to give GalNAc-drosocin 2, which was oxidized with galactose oxidase (Sigma) to the corresponding C-6 aldehyde (isolated yields were >70%). Hydroxylamino derivatives of galactose (3) and GlcNAc (4) were prepared from the corresponding N-hydroxysuccinimidoglycosides using the method of Roy and coworkers.[14] Compounds 3 and 4 were coupled with the glycopeptide aldehyde to give chemoselectively ligated products 5 and 6, respectively (isolated yields were >80%). The glycosylation sequence of glycopeptide 5 mimics that of native drosocin. The glycan in glycopeptide 6 mimics the naturally occurring GlcNAcβ1ø6GalNAc ("core 6") structure; an oxime group substitutes for the natural glycosidic bond and the linkage is extended by one atom.

Unprotected oligosaccharides, either synthetic or derived from natural sources, can be converted to the corresponding glycosylamines via Kochetkov amination.[4k,4l,15] Functionalization of these derivatives with a hydroxylamino group would provide access to a wide variety of oligosaccharide coupling partners. In order to demonstrate this approach we synthesized lactose hydroxylamine 7 by aminooxyacetylation[16] of a glycosylamine derivative. Compound 7 was coupled with the aldehyde derived from enzymatic oxidation of 2 to give chemoselectively ligated glycopeptide 8.

We also applied the enzymatic oxidation and chemoselective ligation reactions to the simple monosaccharide α-benzyl GalNAc to obtain oxime-linked disaccharide 9 for spectroscopic comparison with oxime-linked glycopeptides. Both the trans and cis isomers of the compound 9 were obtained in a ratio of 2.5:1 (trans/cis).[17] $^1$H NMR analysis of drosocin analog 6, bearing an identical oxime-linked disaccharide, revealed only a single isomer which was assigned the trans configuration based on the chemical shift of the oxime proton (HC=NOR, 7.69 ppm). Thus, the C-1 substituent of GalNAc appears to affect the trans/cis ratio of oximes formed at C-6. Conformational analysis of oligosaccharides possessing the native GlcNAcβ1ø6GalNAcα1øOR structure has exposed interactions between the C-1 sustituent of GalNAc and the GlcNAc residue that affect the conformational preference of the β1ø6 linkage.[18]

Finally, we compared the relative potencies of unglycosylated drosocin and chemoselectively ligated analog 5 (the closest structural mimic to native GaløGalNAc-drosocin) to determine the functional consequences of the unnatural oxime-linked glycan at Thr11. Glycopeptide 5 was found to be 3 to 4-fold more potent in blocking bacterial growth (IC$_{50}$=0.12±0.02 μM) than unglycosylated drosocin (IC$_{50}$=0.40±0.05 μM), similar to the trend observed with native glycosylated drosocin. This observation indicates that flexibility in the structure of the outlying glycoform is permitted as long as the native sugar-peptide linkage is maintained. Glycoproteins that follow this paradigm are well suited synthetic targets for this chemoselective ligation approach.

General methods: Galactose oxidase (EC 1.1.3.9) (450 units/mg) was purchased from Sigma. All chemical reagents were obtained from commercial suppliers and used without further purification. For flash chromatography, 230–400 mesh silica gel 60 (E. Merck No. 9385) was employed. Analytical thin layer chromatography (tlc) was conducted on Analtech Uniplate silica gel plates with detection by ceric ammonium molybdate and/or by UV light. Reversed-phase high pressure liquid chromatography (RP-HPLC) was performed on a Rainin Dynamax SD-200 system using Microsorb and Dynamax C$_{18}$ reversed-phase columns (analytical: 4.6 mm ID×25 cm, 1 mL/min; semi-preparative: 10 mm ID×25 cm, 3 mL/min), and ultraviolet detection (230 nm) was performed with a Rainin Dynamax UV-1 detector. The *E. coli* strain D22 used in bacterial growth inhibition assays was obtained from the *E. Coli* Genetic Stock Center at Yale University.

Unless otherwise noted, all air and moisture sensitive reactions were performed under a nitrogen atmosphere. All solvents were distilled under a nitrogen atmosphere prior to use. THF was dried and deoxygenated over Na/benzophenone; CH$_2$Cl$_2$, CH$_3$CN, and benzene were dried over CaH$_2$; toluene was dried over Na. Unless otherwise specified, extracts were dried over MgSO$_4$ and solvents were removed with a rotary vacuum evaporator. The $^{1}$H- and $^{13}$C-NMR spectra were obtained with Bruker AMX-300 and AMX-400 MHz spectrometers. Chemical shifts are reported in δ values downfield from tetramethylsilane (TMS) and coupling constants are reported in Hz. Low resolution FAB mass spectra were obtained by the Mass Spectrometry Laboratory at the University of California at Berkeley on a AE1 M512 mass spectrometer using m-nitrobenzyl alcohol or glycerol as the matrix solvent. Electrospray ionization mass spectrometry (ESI-MS) was performed on a Hewlett-Packard 5989A mass spectrometer equipped with an electrospray ion source. The synthesis of compound 5S is show in Scheme 1c.

Scheme 1c

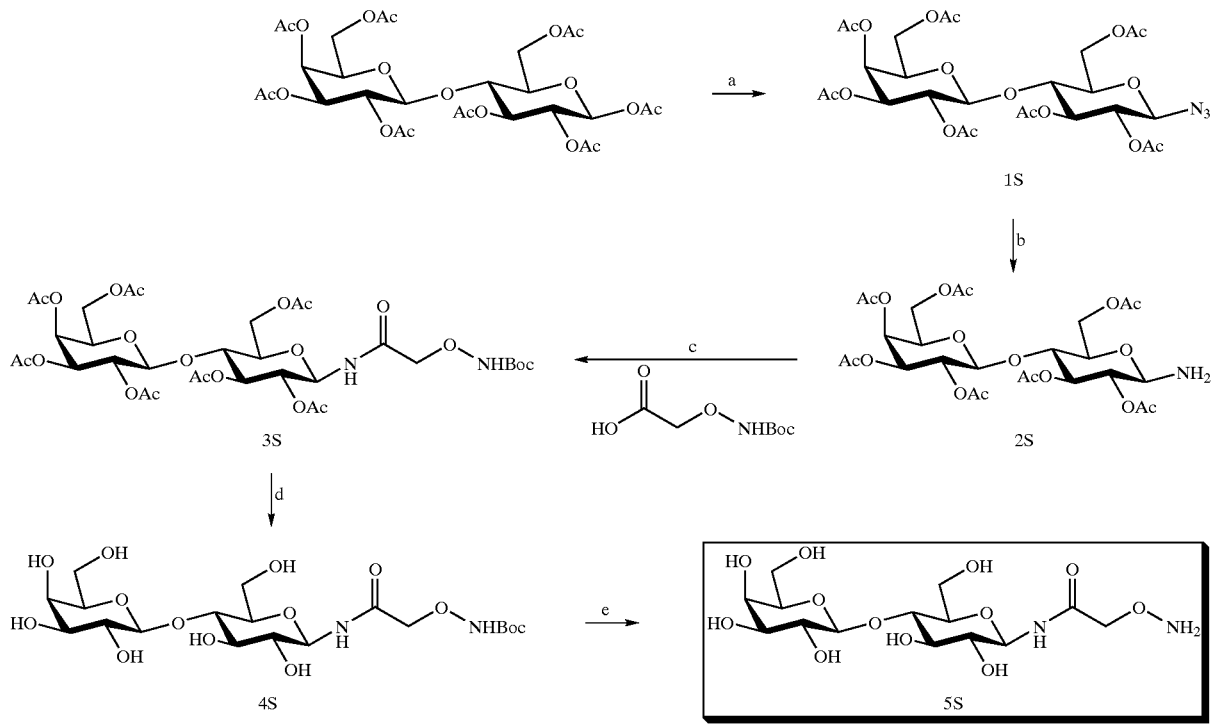

(a) TMSN$_3$, SnCl$_4$, AgClO$_4$; (b) H, 10% Pd/C; (c) HOBt, EDC; (d) N$_2$H$_4$, EtOH; (e) 1:1 TFA/CH$_2$Cl$_2$

4-O-(2,3,4,6-Tetra-O-acetyl-β-D-galactopyranosyl)-2,3,6-tri-O-acetyl-β-D-glucopyranosyl azide (1S). To a suspension of 0.033 g (0.147 mmol) of AgClO$_4$ in 7 mL of CH$_2$Cl$_2$ was added 0.147 mL of a 1 M solution of SnCl$_4$ in CH$_2$Cl$_2$. The solution was stirred for 1 h in the dark at rt. A solution of β-lactose octaacetate (0.500 g, 0.737 mmol) and azidotrimethylsilane (0.117 mL, 0.884 mmol) in CH$_2$Cl$_2$ (7 mL) was added to the suspension and the reaction was stirred for 5.5 h. The mixture was diluted with 50 mL CH$_2$Cl$_2$ and washed with 25 mL saturated aqueous NaHCO$_3$ and water (3×15 mL). The organic layer was dried and concentrated directly onto silica gel for chromatography. The column was eluted with 2:1 hexanes/ethyl acetate to give 0.262 g (54%) of a pale yellow foam; R$_f$ 0.54 (1:3 hexanes/ethyl acetate); IR (KBr pellet): 3446, 2121, 1751,1371, 1232, 1059 cm$^{-1}$; $^{1}$H NMR (300 MHz, CDCl$_3$): δ1.97 (s, 3 H), 2.05 (s, 3 H), 2.06 (s, 3 H), 2.07 (s, 3 H), 2.09 (s, 3 H), 2.14 (s, 3 H), 2.15 (s, 3 H), 3.79 (m, 3 H), 4.11 (m, 3 H), 4.50 (m, 2 H), 4.86 (t, 1 H, J=8.84), 4.95 (dd, 1 H, J=10.45, 3.40), 5.11 (m, 1 H), 5.21 (t, 1 H, J=9.09), 5.35 (d, 1 H, J=2.64); $^{13}$C NMR (100 MHz, CDCl$_3$): δ20.46, 20.60, 20.69, 20.76, 60.76, 61.71, 66.57, 69.06, 70.76, 70.91, 72.52, 74.80, 75.76, 77.21, 87.69, 101.09, 169.02, 169.44, 169.56, 170.00, 170.06, 170.24, 170.29; FAB-MS: Calcd. for C$_{26}$H$_{36}$O$_{17}$N$_3$ 662 (M+H), found 662. Anal. Calcd. for C$_{26}$H$_{35}$O$_{17}$N$_3$: C, 47.20; H, 5.33; N, 6.35. Found: C, 47.49; H, 5.60; N, 6.31.

4-O-(2,3,4,6-Tetra-O-acetyl-β-D-galactopyranosyl)-2,3,6-tri-O-acetyl-β-D-glucopyranosyl amine (2S). A solution of 1S (430 mg, 0.65 mmol) and 10% Pd/C (80 mg) in methanol (20 ml) was stirred under a hydrogen atmosphere for 30 min. The mixture was filtered through Celite and concentrated to give 413 mg (100%) of unstable glycosylamine 2S which was used without further purification in the next reaction.

N$^{α}$-[4-O-(2,3,4,6-Tetra-O-acetyl-β-D-galactopyranosyl)-2,3,6-tri-O-acetyl-β-D-glucopyranosyl]-tert-butoxycarbonylaminooxyacetamide (3S). Crude compound 2S (413, 0.65 mmol) was dissolved in 15 ml of freshly distilled CH$_2$Cl$_2$ along with t-butoxycarbonylaminooxy acetic acid (157 mg, 0.80 mmol), 1-hydroxybenzotriazole hydrate (108 mg, 0.80 mmol), and 1-(3-dimethylaminopropyl)-3-ethylcarbodiimide (153 mg, 0.80 mmol) and stirred at rt for 4.5 h. The reaction solution was diluted with 100 mL of CH$_2$Cl$_2$ and washed with 0.1 M HCl (3×25 mL), water (3×25 mL) and saturated aqueous NaHCO$_3$ (3×25 mL). The organic layer was dried and concentrated directly onto silica gel for chromatography. The column was eluted with 1:1 hexanes/ethyl acetate to give 400 mg (76%) of a white foam. $^{1}$H NMR (400 MHz, CDCl$_3$): δ1.47 (s, 9 H), 1.96 (s, 3 H), 2.02 (s, 3 H), 2.04 (s, 3 H), 2.05 (s, 3 H), 2.06 (s, 3 H), 2.10 (s, 3 H), 2.15 (s, 3 H), 3.82 (m, 3H), 4.11 (m, 3H), 4.33 (dd, 2H, J=25.43, 16.41), 4.47 (m, 2H), 4.94 (m, 2H), 5.10 (dd, 1H, J=7.78, 10.36), 5.28 (m, 2H), 5.34 (d, 1H, J=3.20). $^{13}$C NMR (100 MHz, CDCl$_3$): δ820.50, 20.60, 20.64, 20.72, 20.80, 20.85, 28.09, 60.86, 62.08, 66.63, 69.02, 70.73, 71.02, 71.10, 72.75, 74.60, 75.97, 77.50, 83.14, 100.95, 157.38, 168.99, 169.55, 170.07, 170.15, 170.36, 170.94. FAB-MS: Calcd. for $C_{33}H_{49}O_{21}N_2$ 809 (M+H), found 809.

$N^\alpha$-[(4-O-β-D-galactopyranosyl)-β-D-glucopyranosyl]-tert-butoxycarbonylaminooxyacetamide (4S). To a solution of compound 3S (32 mg, 0.040 mmol) in 3.6 mL MeOH was added 0.40 mL of NaOMe in MeOH (100 mM). The reaction mixture was stirred at rt for 7.5 h, neutralized on H$^+$ resin and concentrated to give 21 mg (100%) of compound 4S. $^1$H NMR (400 MHz, D$_2$O): δ3.71 (m, 14 H), 4.51 (app d, 3H), 5.06 (d, 1 H, J=9.16). $^{13}$C NMR (100 MHz, D$_2$O): δ29.94, 30.05, 32.15, 62.37, 63.58, 71.07, 73.47, 74.02, 75.02, 77.16, 77.52, 77.88, 79.02, 80.26, 81.38, 105.4, 161.2, 174.9.

$N^\alpha$-[(4-O-β-D-galactopyranosyl)-β-D-glucopyranosyl]-aminooxyacetamide (5S). Compound 4S (21 mg, 0.040 mmol) was dissolved in 3:2 CH$_2$Cl$_2$/TFA and stirred at rt for 30 min. The solvent was removed under vacuum and the residue was coevaporated twice with toluene. The crude product was dissolved in water, neutralized on anion exchange resin (hydroxide form) and concentrated to afford 17 mg (100%) of free hydroxylamine 5S. $^1$H NMR (400 MHz, D$_2$O): δ3.73 (m, 14 H), 4.27 (s, 2 H), 4.45 (d, 1 H, J=7.40), 5.07 (d, 1 H, J=9.16). $^{13}$C NMR (100 MHz, D$_2$O): δ62.36, 63.59, 71.10, 73.48, 73.94, 75.04, 76.12, 77.54, 77.90, 79.04, 80.26, 81.42, 105.41, 176.4. FAB-MS: Calcd. for $C_{14}H_{27}O_{12}N_2$ (M+H) 415, found 415.

H$_2$N-Gly-Lys-Pro-Arg-Pro-Tyr-Ser-Pro-Arg-Pro-Thr(α-D-GalNAc)-Ser-His-Pro-Arg-Pro-Ile-Arg-Val-OH (GalNAc-drosocin) (SEQ ID NO:4). The GalNAc-drosocin glycopeptide was synthesized on HMP resin using $N^\alpha$-Fmoc-protected amino acids and DCC-mediated HOBT ester activation in NMP (ABI 431A synthesizer, user-devised cycles). The glycosylated amino acid $N^\alpha$-Fmoc-Thr (Ac$_3$-α-D-GalNAc, 1) (~2×molar excess) was activated with HBTU in the presence of HOBt and DIEA; acylation was complete within 6 h. After completion of peptide synthesis, the sugar moiety was deacetylated by treating the resin with 5.5% hydrazine hydrate in MeOH for 18 h at rt and washing with methanol and diethyl ether. Peptide resin cleavage/deprotection was accomplished with reagent K (4 h, rt) (King, D. S.; Fields, C.; Fields, G. Int. *J. Pep. Prot. Res.* 1990, 36, 225). The purity of the resulting crude glycopeptide was ~95% as assessed by RP-HPLC and ESI-MS: Calcd. 2401.78 (M$^+$), found 2402.13. The drosocin glycopeptide was used without further purification in subsequent reactions. The chemical synthesis of unglycosylated drosocin was accomplished using similar methods.

Galactose oxidase reactions. A solution of GalNAc-drosocin (1 mM) in Dulbecco's phosphate buffer saline, pH 7.3, and galactose oxidase (50 units) was incubated at 37° C. for 1.5 h. Oxidized GalNAc-drosocin was purified by semi-preparative RP-HPLC. Elution was accomplished by a gradient of acetonitrile in water, both with 0.1% TFA: CH$_3$CN:H$_2$O (85:15–70:30) (55 min). The aldehyde product was analyzed by ESI-MS: Calcd. 2399.76, found 2418.29 (M+H$_2$O, hydrated aldehyde).

Chemoselective ligation reactions. A solution of drosocin glycopeptide aldehyde (0.50 mM) in NaOAc buffer (100 mM, pH 5.5) was incubated with compound 3, 4 or 7 (final concentration=1.25 mM) at 37° C. for 24 h. The reactions were monitored by RP-HPLC: elution was accomplished by a gradient of acetonitrile in water, both with 0.1% TFA: CH$_3$CN:H$_2$O (85:15–70:30) (28 min). The respective products 5, 6 and 8 were analyzed by ESI-MS and glycopeptide 6 was further characterized by $^1$H NMR analysis. Glycopeptide 5: Calcd. 2576.92 (M$^+$), found 2577.20. Glycopeptide 6: Calcd. 2618.22 (M$^+$), found 2617.70. Characteristic peak in the $^1$H MMR spectrum (400 MHz, D$_2$O): δ7.69 (d, J=3.2) (HC=NOR). Glycopeptide 8: Calcd. 2796.12 (M$^+$), found 2796.22.

Bacterial growth inhibition assays. Growth inhibition assays were performed essentially as described by Bulet et al. (*Eur. J. Biochem.* 1996, 238, 64). Sterile 96 well plates (Corning #25860) were used, with a final volume of 40 μl per well. This volume comprised 35 μl of a mid-logarithmic phase culture of *E. coli* D22 at an initial $A_{595}$=0.001 in Luria-Bertani (LB) media containing streptomycin (50 μg/ml), added to 5 μl serially diluted peptide (unglycosylated drosocin or GalGalNAc-drosocin) in water. Peptide concentrations were determined by measuring dry weight, and assuming 80% of that weight was peptide and the remainder water and salts. Final concentrations ranged from $10^{-11}$ to $10^{-2}$ M; the precise range used for a given peptide depended on its potency. Plates were incubated for 6 h at 25° C. with periodic shaking. Growth was determined by measuring the absorbance at 595 nm on a BioRad 550 microplate reader. Percent inhibition was defined as (($A_o - A_x$)/$A_o$)*100), where $A_o$ was the absorbance of a control well lacking peptide and $A_x$ was the absorbance of a well with peptide.

REFERENCES 1. (a) Bill, R. M.; Flitsch, S. L. *Chem. Biol.* 1996, 3, 145. (b) Lis, H.; Sharon, N. *Eur. J. Biochem.* 1993, 218, 1. (c) Cumming, D. A. *Glycobiology* 1991, 1, 115.
2. (a) Varki, A. *Glycobiology* 1993, 3, 97. (b) Snell, W. J.; White, J. M. *Cell* 1996, 85, 629. (c) Lasky, L. A. *Annu. Rev. Biochem.* 1995, 64, 113. (d) Sears, P.; Wong, C. -H. *Proc. NatL. Acad. Sci. USA* 1996, 93, 12086.
3. (a) O'Connor, S. E.; Imperiali, B. *Chem. Biol.* 1996, 3, 803. (b) Rickert, K. W.; Imperiali, B. *Chem. Biol.* 1995, 2, 751. (c) Wyss, D. F.; Choi, J. S.; Li, J.; Knoppers, M. H.; Willis, K. J.; Arulanandam, A. R. N.; Smolyar, A.; Reinherz, E. L.; Wagner, G. *Science* 1995, 269, 1273. (d) Gowda, D. C.; Jackson, C. M.; Kurzban, G. P.; McPhie, P.; Davidson, E. A. *Biochemistry* 1996, 35, 5833. (e) Garone, L.; Edmunds, T.; Hanson, E.; Bernasconi, R.; Huntington, J. A.; Meagher, J. L.; Fan, B.; Gettins, P. G. W. *Biochemistry* 1996, 35, 8881. (f) Live, D. H.; Kumar, R. A.; Beebe, X.; Danishefsky, S. J. *Proc. Natl. Acad. Sci. USA* 1996, 93, 12759.
4. (a) Roberge, J. Y.; Beebe, X.; Danishefsky, S. J. *Science* 1995, 269, 202. (b) Cohen-Anisfeld, S. T.; Lansbury, P. T., Jr. *J. Am. Chem. Soc.* 1993, 115, 10531. (c) Meldal, M.; Bock, K. *Glycoconjugate J.* 1994, 11, 59. (d) Meldal, M. *Curr. Opin. Struct. Biol.* 1994, 4, 710. (e) Paulsen, H.; Schleyer, A.; Mathieux, N.; Meldal, M.; Bock, K. *J. Chem. Soc., Perkin Trans. 1* 1997, 281. (f) Bielfeldt, T.; Peters, S.; Meldal, M.; Bock, K.; Paulsen, H. *Angew. Chem. Int. Ed. Engl.* 1992, 31, 857. (g) Meinjohanns, E.; Meldal, M.; Schleyer, A.; Paulsen, H.; Bock, K. *J. Chem. Soc., Perkin Trans. 1* 1996, 9985. (h) Ciommer, M.; Kunz, H. *Synlett* 1991, 593. (i) Nakahara, Y.; Nakahara, Y.; Ogawa, T. *Carbohydr. Res.* 1996, 292, 71. (j) Polt, R.; Szabó, L.; Treiberg, J.; Li, Y.; Hruby, V. J. *J. Am. Chem. Soc.* 1992, 114, 10249. (k) Anisfeld, S. T.; Lansbury, P. T., Jr. *J. Org. Chem.* 1990, 55, 5560. (l) Vetter, D.; Gallop, M. A. *Bioconjugate Chem.* 1995, 6, 316.
5. (a) Witte, K.; Sears, P.; Martin, R.; Wong, C. -H. *J. Am. Chem. Soc.* 1997, 119, 2114. (b) Schuster, M.; Wang, P.; Paulson, J. C.; Wong, C.-H. *J. Am. Chem. Soc.* 1994, 116, 1135. (c) Wong, C.-H.; Schuster, M.; Wang, P.; Sears, P. *J. Am. Chem. Soc.* 1993, 115, 5893. (d) Wang, L. -X.; Fan, J. -Q.; Lee, Y. C. *Tetrahedron Lett.* 1996, 37, 1975. (e) Imperiali, B.; Rickert, K. W. *Proc. NatL. Acad. Sci. USA* 1995, 92, 97.

6. (a) Muir, T. W. *Structure* 1995, 3, 649. (b) Hilvert, D. *Chem. Biol.* 1994, 1, 201. (c) Canne, L. E.; Ferré-D'Amaré, A. R.; Burley, S. K.; Kent, S. B. H. *J. Am. Chem. Soc.* 1995, 117, 2998. (d) Lu, W.; Qasim, M. A.; Kent, S. B. H. *J. Am. Chem. Soc.* 1996, 118, 8518. (e) Shao, J.; Tam, J. P. *J. Am. Chem. Soc.* 1995, 117, 3893. (f) Liu, C. -F.; Rao, C.; Tan, J. P. *J. Am. Chem. Soc.* 1996, 118, 307. (g) Rose, K. *J. Am. Chem. Soc.* 1994, 116, 30. (h) Rose, K.; Zeng, W.; Regamey, P. -O.; Chernushevich, I. V.; Standing, K. G.; Gaertner, H. F. *Bioconjugate Chem.* 1996, 7, 552.
7. (a) Amaral, D.; Bernstein, L.; Morse, D.; Horecker, B. L. *J. Biol. Chem.* 1963, 238, 2281. (b) Gahmberg, C. G.; Tolvanen, M. *Meth. Enzymol.* 1994, 230, 32.
8. *Molecular Glycobiology;* Fukuda, M. and Hindsgaul, O., Eds.; Oxford University: Oxford, 1994.
9. (a) Andreotti, A. H.; Kahne, D. *J. Am. Chem. Soc.* 1993, 115, 3352. (b) The second sugar attached to a glycopeptide may also play an important role in defining the local conformation. Liang, R.; Andreotti, A. H.; Kahne, D. *J. Am. Chem. Soc.* 1995, 117, 10395. (c) Gerken, T. A.; Butenhof, K. J.; Shogren, R. *Biochemistry* 1989, 28, 5536. (d) Shogren, R.; Gerken, T. A.; Jentoft, N. *Biochemistry* 1989, 28, 5525.
10. (a) Stowell, C. P.; Lee, Y. C. *Adv. Carbohydr. Chem. Biochem.* 1980, 37, 225. (b) Wong, S. Y. C.; Guile, G. R.; Dwek, R. A.; Arsequell, G. *Biochem. J.* 1994, 300, 843.
11. (a) Cervigni, S. E.; Dumy, P.; Mutter, M. *Angew. Chem. Int. Ed. Engl.* 1996, 35, 1230. (b) Zhao, Y.; Kent, S. B. H.; Chait, B. T. *Proc. Natl. Acad. Sci. USA* 1997, 94, 1629.
12. (a) Bulet, P.; Dimarcq, J. -L.; Hetru, C.; Lagueux, M.; Charlet, M.; Hegy, G.; Van Dorsselaer, A.; Hoffinan, J. A. *J. Biol. Chem.* 1993, 268, 14893. (b) Bulet, P.; Urge, L.; Ohresser, S.; Hetru, C.; Otvos, L., Jr. *Eur. J. Biochem.* 1996, 238, 64.
13. The position of the linkage has not been directly determined but is suggested to be 1ø3 (ref. 12b).
14. Cao, S.; Tropper, F. D.; Roy, R. *Tetrahedron* 1995, 51, 6679.
15. Likhosherstov, L. M.; Novikova, O. S.; Derevitskaja, V. A.; Kochetkov, N. K. *Carbohydr. Res.* 1986, 146, C1.
16. Kurth, M.; Pelegrin, A.; Rose, K.; Offord, R. E.; Pochon, S.; Mach, J. -P.; Buchegger, F. *J. Med. Chem.* 1993, 36, 1255.
17. The trans and cis isomers of compound 9 were assigned based on the chemical shift of the oxime proton (HC=NOR) in the $^1$H NMR spectrum (400 MHz, $D_2O$) (Karabatsos, G. J.; Hsi, N. *Tetrahedron* 1967,23,1079). Trans isomer: 7.56 ppm(doublet, J=4.2 Hz); Cis isomer: 6.95 ppm (doublet, J=4.4 Hz).
18. Pollex-Krfiger, A.; Meyer, B.; Stuike-Prill, R.; Sinnwell, V.; Matta, K. L.; Brockhausen, I. *Glycoconjugate J.* 1993, 10, 365.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A peptide comprising a (2S)-aminolevulinic acid residue comprising a substituted or unsubstituted ketone group.

2. The peptide according to claim 1, wherein the ketone group of the residue is substituted.

3. The peptide according to claim 1, wherein the ketone group of the residue is substituted with a detectable label.

4. The peptide according to claim 1, wherein the ketone group of the residue is substituted with a detectable label comprising a fluorescent resonance energy transfer (FRET) donor or acceptor.

5. The peptide according to claim 1, wherein the ketone group of the residue is substituted with an O- or N-linked glycosyl group to yield glycoconjugate.

6. The peptide according to claim 1, wherein the ketone group of the residue is substituted with an aminooxy sugar to yield corresponding oxime.

7. The peptide according to claim 1, wherein the ketone group of the residue is substituted with an aminooxy sugar consisting of aminooxy N-acetyl glucosamine (GalNAc).

8. The peptide according to claim 1, wherein the ketone group of the residue is substituted with an aminooxy sugar consisting of aminooxy lactose.

9. The peptide according to claim 1, wherein the ketone group of the residue is substituted with a hydrazide sugar to yield a corresponding hydrazone.

10. The peptide according to claim 1, wherein the ketone group of the residue is substituted with a hydrazide sugar consisting of lactose succinic hydrazide.

11. The peptide according to claim 1, wherein the ketone group of the residue is substituted with a thiosemicarbazide-functionalized sugar to yield a corresponding thiosemicarbazone.

12. The peptide according to claim 1, wherein the ketone group of the residue is substituted with a thiosemicarbazide-functionalized sugar consisting of chitobiose thiosemicarbazide.

13. The peptide according to claim 1, wherein the ketone group of the residue is substituted with a thiosemicarbazide-functionalized sugar consisting of lactose thiosemicarbazide.

14. The peptide according to claim 1, wherein the peptide is in vitro.

15. The peptide according to claim 2, wherein the peptide is in vitro.

16. The peptide according to claim 3, wherein the peptide is in vitro.

17. The peptide according to claim 4, wherein the peptide is in vitro.

18. The peptide according to claim 5, wherein the peptide is in vitro.

19. The peptide according to claim 6, wherein the peptide is in vitro.

20. The peptide according to claim 7, wherein the peptide is in vitro.

21. The peptide according to claim 8, wherein the peptide is in vitro.

22. The peptide according to claim 9, wherein the peptide is in vitro.

23. The peptide according to claim 10, wherein the peptide is in vitro.

24. The peptide according to claim 11, wherein the peptide is in vitro.

25. The peptide according to claim 12, wherein the peptide is in vitro.

26. The peptide according to claim 13, wherein the peptide is in vitro.

27. The peptide according to claim 1, wherein the peptide is in incorporated into a cell or cellular structure.

* * * * *